United States Patent
Phillips et al.

(10) Patent No.: US 9,937,197 B2
(45) Date of Patent: *Apr. 10, 2018

(54) WOUND HEALING COMPOSITIONS AND TREATMENTS

(71) Applicant: CoDa Therapeutics, Inc., San Diego, CA (US)

(72) Inventors: Anthony Phillips, San Diego, CA (US); David Eisenbud; Scott Bannan, San Diego, CA (US); Grove Matsuoka, San Diego, CA (US); David Pool, San Diego, CA (US); Tracey Sunderland, San Diego, CA (US); Bradford Duft, San Diego, CA (US)

(73) Assignee: CoDa Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/076,513

(22) Filed: Mar. 21, 2016

(65) Prior Publication Data

US 2016/0339052 A1 Nov. 24, 2016

Related U.S. Application Data

(63) Continuation of application No. 14/214,922, filed on Mar. 15, 2014, now Pat. No. 9,290,554, which is a continuation of application No. 13/844,762, filed on Mar. 15, 2013, now Pat. No. 9,156,896.

(51) Int. Cl.

| | |
|---|---|
| C12N 15/113 | (2010.01) |
| A61K 31/713 | (2006.01) |
| A61K 9/06 | (2006.01) |
| A61K 47/38 | (2006.01) |
| A61K 9/70 | (2006.01) |
| A61K 31/7088 | (2006.01) |
| A61B 5/107 | (2006.01) |
| A61B 5/11 | (2006.01) |
| A61B 5/00 | (2006.01) |
| C07K 14/47 | (2006.01) |
| A61K 47/00 | (2006.01) |
| A61K 9/00 | (2006.01) |
| A61K 48/00 | (2006.01) |
| A61K 31/7105 | (2006.01) |
| A61K 47/10 | (2017.01) |

(52) U.S. Cl.
CPC ........ *A61K 31/7088* (2013.01); *A61B 5/0064* (2013.01); *A61B 5/0077* (2013.01); *A61B 5/1072* (2013.01); *A61B 5/1079* (2013.01); *A61B 5/1109* (2013.01); *A61B 5/445* (2013.01); *A61B 5/4839* (2013.01); *A61B 5/4848* (2013.01); *A61B 5/7275* (2013.01); *A61K 9/0014* (2013.01); *A61K 9/06* (2013.01); *A61K 9/70* (2013.01); *A61K 31/7105* (2013.01); *A61K 47/00* (2013.01); *A61K 47/10* (2013.01); *A61K 47/38* (2013.01); *A61K 48/00* (2013.01); *C07K 14/47* (2013.01); *C12N 15/1138* (2013.01); *A61B 2503/40* (2013.01); *C12N 2310/11* (2013.01); *C12N 2310/14* (2013.01); *C12N 2320/30* (2013.01); *C12N 2320/35* (2013.01)

(58) Field of Classification Search
None
See application file for complete search history.

(56) References Cited

U.S. PATENT DOCUMENTS

| | | |
|---|---|---|
| 5,593,974 A | 1/1997 | Rosenberg et al. |
| 2005/0119211 A1 | 6/2005 | Bharat et al. |

FOREIGN PATENT DOCUMENTS

| | | |
|---|---|---|
| CN | 102105492 A | 6/2011 |
| WO | WO-2005/053600 A2 | 6/2005 |
| WO | WO-2008/060622 A2 | 5/2008 |
| WO | WO-2009/075882 A2 | 6/2009 |
| WO | WO-2009/085268 A2 | 7/2009 |
| WO | WO-2009/097077 A2 | 8/2009 |

OTHER PUBLICATIONS

Becker et al., "Connexins in wound healing; perspectives in diabetic patients", Biochemica et Biophysica Acta (BBA)—Biomembranes, 1818(8):2068-2075 (2011).
Chang et al., "Antisense down regulation of connexin31.1 reduces apoptosis and increases thickness of human and animal corneal epithelia", Cell Biology Internatinal, 33(3):376-385 (2009).
Di Micco et al., "Surgical injury of rat arteries: genetic control of the remodeling process", European Journal of Cardio-Thoracic Surgery, 22(2):266-270, (2002).
Fonder et al., "Treating the chronic wound: A practical approach to the care of nonhealing wounds and wound care dressings", Journal of the American Academy of Dermatology, 58(2):185-206, (2008).
Gethin, "The importance of continuous wound measuring", Wounds UK, 2(2):60-68, (2006).
Gilmartin et al., "Integration of Scaffolds into Full-Thickness Skin Wounds: The Connexin Response", Advanced Healthcare Materials, 2(8):1151-1160, (2013).
Herberger et al., "Efectiveness, Tolerability, and Safety of Electrical Stimulaiton of Wounds with an Electrical Stimulation Device: Results of a Retrospective Register Study", Wounds, 24(4):76-84, (2012).
Liu et al., "Synergistic effect of chemical penetration enhancer andiontophoresis on transappendageal transport of oligodeoxynucleotides", International Journal of Pharmaceutics, 441(1-2):687-69, (2012).

(Continued)

*Primary Examiner* — Tracy Vivlemore
(74) *Attorney, Agent, or Firm* — Duane Morris LLP

(57) ABSTRACT

This invention concerns improved methods, uses, and kits for treating chronic wounds through the administration of anti-connexin agents, particularly anti-connexin 43 antisense polynucleotides. The methods, uses, and kits of the invention are based on the surprising and unexpected discovery that chronic wounds that do not increase or decrease in size by more than a pre-determined amount during a pre-treatment phase are more amenable to successful treatment than wounds whose size varies outside the target range during the pre-treatment phase.

33 Claims, 6 Drawing Sheets

(56) References Cited

OTHER PUBLICATIONS

Office Action, from corresponding Chinese Patent Application No. 2014800285080, dated Mar. 3, 2017, 10 pages.
Ormonde et al., "Regulation of Connexin43 Gap Junction Protein Triggers Vascular Recovery and Healing in Human Ocular Persistent Epithelial Defect Wounds", Journal of Membrane Biology, 245(7):381-388 (2012).
Supplementary European Search Report, dated Mar. 22, 2017, from corresponding European Patent Application No. EP14764924, 26 pages.
Yoon et al., "A novel method of organotypic brain slice culture using connexin-specific antisense oligodeoxynucleotides to improve neuronal survival", Brain Research, 1353(31): 194-203 (2010).
Kirsner, R.S., et al., "Spray-applied cell therapy with human allogeneic fibroblasts and keratinocytes for the treatment of chronic venous leg ulcers: a phase 2, multicentre, double-blind, randomised, placebo-controlled trial," The Lancet, Sep. 15, 2012, vol. 380, No. 9846, p. 977-985.
Harding, K.G., et al., "Efficacy and safety of the freeze-dried cultured human keratinocyte lysate, LyphoDerm (TM) 1.9%, in the treatment of hard-to-heal venous leg ulcers," Wound Repair and Regeneration, 2005, vol. 13, No. 2, p. 138-147.

FIGURE 1C

|  | 3.0 mg/mL vs. V+SOC | 3.0 mg/mL vs. V | 3.0 mg/mL vs. SOC | 1.0 mg/mL vs. V+SOC | 1.0 mg/mL vs. V | 1.0 mg/mL vs. SOC |
|---|---|---|---|---|---|---|
|  | Delta P-value | | | | | |
| Surface Area Reduction | 6.4% 0.249 | 4.0% 0.319 | 19.6% 0.457 | -11.8% 0.726 | -14.2% 0.435 | -1.4% 0.477 |
| Time to 100% closure | 0.320 | 0.342 | 0.843 | 0.125 | 0.111 | 0.694 |
| Incidence of Complete Healing | 6% 0.233 | 1% 0.427 | 19% 0.192 | -14% 0.268 | -19% 0.139 | -1% 0.912 |

FIGURE 4

| (Delta / p values) | 3.0 mg/mL vs. V+SOC | 3.0 mg/mL vs. V | 3.0 mg/mL vs. SOC | 1.0 + 3.0 mg/mL vs. V+SOC | 1.0 mg/mL vs. V+SOC | 1.0 mg/mL vs. V | 1.0 mg/mL vs. SOC |
|---|---|---|---|---|---|---|---|
| Surface Area Reduction | 20.3% / 0.037 | 20.3% / 0.026 | 22.4% / 0.443 | 9.1% / 0.052 | 3.7% / (NA) | 3.7% / 0.320 | 5.8% / 0.610 |
| Time to 100% closure (K-M ; hazard ratio) | 1.8 / 0.050 | 1.8 / 0.057 | *** | 0.050 | NA | NA | NA |
| Incidence of Complete Healing | 18% / 0.013 | 15% / 0.018 | 26% / 0.104 | 8% / 0.050 | -1% / (NA) | -4% / 0.374 | +7% / 0.872 |

```
                          SEQUENCE LISTING

<160> NUMBER OF SEQ ID NOS: 7

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtaattgcgg caagaagaat tgtttctgtc                                          30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtaattgcgg caggaggaat tgtttctgtc                                          30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcaagagac accaaagaca ctaccagcat                                          30

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcctgagcaa tacctaacga acaaata                                             27

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgtccgagcc cagaaagatg aggtc                                               25
```

```
<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tttcttttct atgtgctgtt ggtga                                           25

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gacagaaaca attcctcctg ccgcatttac                                      30
```

WOUND HEALING COMPOSITIONS AND TREATMENTS

CROSS-REFERENCE TO RELATED APPLICATIONS

This application is a continuation of U.S. application Ser. No. 14/214,922, filed on Mar. 15, 2014, which will issue as U.S. Pat. No. 9,290,554 on Mar. 22, 2016, which is a continuation of U.S. application Ser. No. 13/844,762, filed on Mar. 15, 2013 and issued as U.S. Pat. No. 9,156,896 on Oct. 13, 2015, the entire contents of each of which are hereby incorporated by reference.

FIELD OF THE INVENTION

The inventions relate to methods of identifying and treating refractory chronic wounds that do not heal at expected rates, and dose regimens and articles of manufacture comprising gap junction modulators useful for treating those wounds.

BACKGROUND

The following includes information that may be useful in understanding the present invention. It is not an admission that any of the information provided herein is prior art, or relevant, to the presently described or claimed inventions, or that any publication or document that is specifically or implicitly referenced is prior art.

In humans and other mammals, wound injury triggers an organized complex cascade of cellular and biochemical events that will in most cases result in a healed wound. An ideally healed wound is one that restores normal anatomical structure, function, and appearance at the cellular, tissue, organ, and organism levels. Wound healing, whether resulting from trauma, microbes, or foreign materials, proceeds via a complex process encompassing a number of overlapping phases, including inflammation, epithelialization, angiogenesis, and matrix deposition. Normally, these processes lead to a mature wound and a certain degree of scar formation. Although inflammation and repair mostly occur along a prescribed course, the sensitivity of the process is dependent on the balance of a variety of wound healing modulating factors, including, for example, a complex network of regulatory cytokines and growth factors.

Gap junctions are cell membrane structures that facilitate direct cell-cell communication. A gap junction channel is formed of two connexons (hemichannels), each composed of six connexin subunits. Each hexameric connexon docks with a connexon in the opposing membrane to form a single gap junction. Gap junction channels are reported to be found throughout the body.

Connexins are a family of proteins, commonly named according to their molecular weight or classified on a phylogenetic basis into alpha, beta, and gamma subclasses. At least 20 human and 19 murine isoforms have been identified. Different tissues and cell types are reported to have characteristic patterns of connexin protein expression.

Antisense technology has been reported for the modulation of the expression for genes implicated in viral, fungal, and metabolic diseases. See, e.g., U.S. Pat. Nos. 5,166,195, 5,004,810. Antisense technology has also been developed to modulate connexins and treat wounds. See, e.g., U.S. Pat. Nos. 7,098,190, 7,879,811, 7,902,164, 7,919,474, 8,034,789, 8,059,486, 8,063,023, 8,181,580, and 8,314,074. Peptide inhibitors of gap junctions and hemichannels have also been reported. See, e.g., WO2006/134494, published U.S. patent application publication no. 20100279921.

Despite advances in the understanding of the principles underlying the wound healing process, there remains a significant unmet need in suitable therapeutic options for chronic wound care. These inventions address this continuing need.

BRIEF SUMMARY

The inventions described and claimed herein have many attributes and embodiments including, but not limited to, those set forth or described or referenced in this summary section, which is not intended to be all-inclusive. The inventions described and claimed herein are not limited to or by the features or embodiments identified in this summary section, which is included for purposes of overview illustration only and not limitation.

This disclosure relates to methods of identifying and treating refractory chronic wounds, and dose regimens and articles of manufacture useful for treating those wounds. Pharmaceutical compositions comprising the articles of manufacture, and useful in the methods disclosed herein comprise effective doses of anti-connexin polynucleotides (e.g., a connexin antisense oligodeoxynucleotide such as a single-stranded anti-connexin oligodeoxynucleotide) to connexin 26, connexin 30 and/or connexin 43, as well as other connexins as disclosed herein.

As used herein, in one embodiment of the invention, and by way of example, refractory wounds are chronic wounds, or wounds that do not heal at expected rates, such as delayed-healing wounds and incompletely healing wounds, which do not decrease in size by more than about 30% (+30%) over a standard-of-care treatment period using, for example, compression bandaging or off-loading devices, over about two to four weeks and which do not increase in wound size by more than 15% (−15%). This standard-of-care treatment period may also be referred to as a "run-in" or "pretreatment" period. The increase or decrease in wound size may be referred to broadly as "surface area reduction" (also referred to as SAR"). The SAR range during run-in, e.g., −15% to +30%, may be referred to as the run-in SAR range. Upon presentation of a chronic wound for treatment, standard-of-care is provided for a two to four week period. Estimates and/or formal measurements of the size of the wound upon presentation, and at the end of the run-in period are used to determine if the wound is refractory to standard of care treatment by assessing whether it falls with a designated SAR run-in range. In some aspects, standard of care during the run-in period is multi-layer compression bandaging, for example. In other aspects, the standard of care is off-loading, for example. In some embodiments, the standard of care treatment during the run-in period is single-layer compression bandaging, or a compression stocking. Compression bandages are typically changed or reapplied approximately once per week. In other embodiments, the standard of care treatment during the run-in period is reduction of pressure, or offloading. Foot pressures, shock, and shear may be reduced with appropriately fitted shoes, insoles, and socks. Total non-weight bearing using a wheelchair or crutches is another effective method of relieving pressure. Other off-loading standard of care modalities include total contact casts, removal casts, and removable cast walkers.

In other embodiments, refractory wounds are chronic wounds, or wounds that do not heal at expected rates, such as delayed-healing wounds and incompletely healing wounds, which do not decrease in size by more than about 30% (+30%) over a standard-of-care treatment period using compression bandaging over about two to four weeks.

In still other embodiments, refractory wounds are chronic wounds, or wounds that do not heal at expected rates, such as delayed-healing wounds and incompletely healing wounds, which do not decrease in size by more than about 35% (+35%) over a standard-of-care treatment period using compression bandaging which do not increase in wound size by more than 15% (−15%).

In further embodiments, refractory wounds are chronic wounds, or wounds that do not heal at expected rates, such as delayed-healing wounds and incompletely healing wounds, which do not increase or decrease in size by more than about −5%/+30%, −10%/+30%, −15%/+30%, −20%/+30%, 25%/+30% or −30%/+30%, over a standard-of-care treatment period using compression bandaging over about two to four weeks.

It has been surprisingly observed that the refractory chronic wounds are susceptible to administration of pharmaceutical compositions comprising a pharmaceutically acceptable carrier suitable for topical administration and, for example, from about 0.5 mg/mL to about 40 mg/mL, or by way of additional example from about 1 to 30 mg/mL, of an anti-connexin 26, anti-connexin 30 or anti-connexin 43 polynucleotide.

Accordingly, in one aspect, this disclosure relates to a method of treating a refractory wound, the method comprising:

determining a size of a chronic wound upon initial presentation for treatment to obtain a first size measurement or estimation;

administering standard-of-care, such as, for example, compression bandaging and/or off-loading, to the wound;

determining the size of the wound about 2-4 weeks after administering said standard-of-care to obtain a second size measurement;

determining that the second size indicator of the wound is within a predetermined range (for example, −15 to +30%/−35% to +30%) of the first size measurement, or that it has not healed by more a predetermined amount (e.g., a wound SAR of more than about +30-35%) thereby identifying a refractory wound; and administering at or in proximity to the wound a pharmaceutical composition comprising an effective amount of an anti-connexin 43 polynucleotide, for example. Examples of suitable doses, dose amounts and dose concentrations and formulations are described herein.

The size of the wound may be determined by various methods known in the art, including, for example, by a measurement or reasonable estimation or approximation of any physical dimension of the wound, such as surface area, length of the longest diameter and/or length of the longer perpendicular bisector to the longest diameter. For deep wounds with a relatively small surface area, such as a diabetic foot ulcers, volume may also be used as the size measurement. Other known wound measurement methods include planimetry, wound tracing, digitizing techniques, and stereophotogrammetry, as well as simple ruler-based methods. Three commercially available wound measurement techniques include the Visitrak system (Smith and Nephew Healthcare, Hull, U.K.), a digital photography and image processing system (Analyze, version 6.0; Analyze-Direct, Lenexa, Kans.), and an elliptical measurement method using the standard formula (nab) for the calculation of the area of an ellipse.

In another aspect, this disclosure relates to methods of detecting a refractory chronic wounds susceptible to treatment by pharmaceutical compositions comprising, for example, from about 0.5 mg/mL to about 40 mg/mL or from about 1 to 30 mg/mL of, for example, an anti-connexin 43 polynucleotide, the method comprising measuring a size indicator of a wound upon initial presentation for treatment to obtain a first size measurement;

administering standard-of-care, such as, for example, compression bandaging and/or off-loading, to the wound;

measuring the area of the wound about 2-4 weeks after administering initiating standard of care treatment to obtain a second size measurement;

determining that the second size indicator of the wound is within a predetermined range of the first size measurement as described herein, thereby detecting a slowly progressing or refractory wound susceptible to treatment by administration of a pharmaceutical composition comprising a therapeutically effective amount of, for example, an anti-connexin 43 polynucleotide. Other connexin targets are contemplated as described herein.

In another aspect, this disclosure relates to kits, packages and/or articles of manufacture useful in treating a subject having a refractory wound, comprising a receptacle containing a pharmaceutical composition comprising an anti-connexin 43 antisense oligodeoxynucleotide present at a therapeutically effective amount or concentration, e.g., from 1.0 to 3.0 to about 30.0 to 100 milligrams per milliliter, and a pharmaceutically acceptable carrier, e.g., a nonionic polyoxyethylene-polyoxypropylene copolymer; and instructions for use of the compositions as described and claimed herein. Such medicaments include those for the treatment of a subject as described herein.

In another aspect this invention relates to a method of detecting a refractory wound with an increased likelihood of complete closure following topical administration to the wound of a composition comprising a nonionic polyoxyethylene-polyoxypropylene copolymer, e.g., poloxamer 407 (at a concentration, for example, of about 15-30%, such as 25-27%) and a single-stranded anti-connexin 43 antisense oligodeoxynucleotide, for example, present at a concentration from about 3.0 to about 30 milligrams per milliliter, or from about 1.0 to about 100 milligrams per milliliter, for example, the method comprising:

measuring a size indicator of a wound upon initial presentation for treatment to obtain a first size measurement;

administering standard-of-care, such as, for example, compression bandaging and/or off-loading, to the wound;

measuring the size indicator of the wound about 2-4 weeks after initiating the standard of care treatment to obtain a second size measurement; and detecting that the area of the wound is within a predetermined size range, for example from about −15% to +30% of its size after the run-in period, thereby determining an increased likelihood of complete closure following topical administration to the refractory wound of a composition comprising said anti-connexin 43 antisense oligodeoxynucleotide.

In some embodiments, the pharmaceutical composition comprises an effective amount of a 3-30 mg/mL or 1-100 mg/mL anti-connexin 43 polynucleotide or other suitable doses disclosed herein. The pharmaceutical composition may further comprise one or more pharmaceutical carriers suitable for topical administration. In one embodiment, the pharmaceutical composition may comprise about 20-30% nonionic polyoxyethylene-polyoxypropylene copolymer, and/or other pharmaceutical carriers disclosed herein.

In one aspect the anti-connexin polynucleotide may be present in the pharmaceutical composition at a concentration of from about 3.0 to about 30 mg/mL, or from about 1.0 to about 100 mg/mL. In some aspects, the anti-connexin polynucleotide may be present at a concentration of about 3, about 5, about 10, or about 30 mg/ml, or any amount up to about 100 mg/mL. In other aspects the anti-connexin polynucleotide may be present in the pharmaceutical composition at a concentration of from about 100 µM to about 5000 µM, for example. In some embodiments, a therapeutically effective amount of a composition of the invention comprises a pharmaceutically acceptable carrier and an anti-connexin agent such as a single-stranded anti-connexin 43 oligodeoxynucleotide present at a concentration from about 0.5 to about 40 mg per milliliter (mL; mg/mL) or from about 3 to about 30 mg/mL, or from about 100 µM to about 5000 µM.

One or more doses may be administered to a subject having a refractory wound. In some embodiments, one or more doses of the pharmaceutical composition may be repeatedly administered at appropriate or desired intervals. In some embodiments, the pharmaceutical composition may be administered repeatedly, for example, daily, or one to six times per week. For example, the anti-connexin agent-containing compositions and formulations described herein can be administered once per week until healing is seen to be proceeding or is complete, as desired. Compositions of the invention may also be applied more frequently, for example, two or three times/week. They may also be applied biweekly, or monthly. The frequency of administration and dose may change over the course of treatment as the wound area and volume change. In addition, further application(s) can be made in the event wound healing once again becomes stalled or delayed.

According to another aspect of the present invention, wound re-epithelialization and/or formation of granulation tissue is promoted. Methods of promoting re-epithelialization of skin wounds comprise administering to a subject having a wound that is not healing at the expected rate, including, for example, a delayed healing or an incompletely healing wound or a chronic wound, an anti-connexin agent, e.g., an anti-connexin polynucleotide, in an amount effective to promote re-epithelialization. Analogous methods can be used to regulate epithelial basal cell division and growth.

It has been surprisingly observed that the refractory wounds are susceptible to administration of pharmaceutical compositions comprising from 0.5 to 40 mg/mL anti-connexin polynucleotide, for example, or higher concentrations, at or in proximity to the wound a pharmaceutical composition comprising and a pharmaceutically acceptable carrier suitable for topical administration. Detecting refractory wounds may advantageously be used to identify patients amenable to treatment with pharmaceutical compositions comprising from 0.5 to 40 mg/mL anti-connexin polynucleotide, e.g., from 3 to 30 mg/mL of anti-connexin 43 ODN, by way of example. Other suitable doses and dose concentrations are provided herein.

In some aspects of the methods of this invention, as noted above, the size of a patient's wound is assessed by ascertaining length, width, depth, edge circumference, volume, or surface area of the wound, or function thereof. Any suitable method may be used, including direct manual measurement, a laser scanner, an imaging device such as a camera, computer tablet or PDA, surface mapping, etc. The currently preferred metric for wound size is wound surface area, preferably obtained as the product of wound length multiplied by wound width, wound tracing, or by planimetry.

Size changes during the run-in period surprisingly and unexpectedly have been discovered to range from an increase in wound size by not more than about 30% to a decrease in wound size by not more than 15% during the run in period, for example, and other ranges and/or threshold amounts as previously noted. Preferred run-in phases range from about 7 to about 30 days, preferably from about 7 days to about 21 days, even more preferably from about 7 days to about 14 days. A 14-day run-in is preferred.

These and other aspects of the present inventions, which are not limited to or by the information in this Brief Summary, are provided below.

BRIEF DESCRIPTION OF THE DRAWINGS

FIGS. 1A-C show the results from a Phase 2B clinical study using a −40% to +40% wound size change during the run in period following a 10 week treatment period. FIG. 1A shows the plot for % complete wound closure the patients in each study arm: standard of care (SOC), vehicle alone, and low dose (1 mg) or high dose (1 mg) of an exemplary anti-connexin 43 polynucleotide. FIG. 1B shows the plot for wound surface area reduction for patients in each study arm. FIG. 1C shows that patients selected based on the −40% to +40% wound size change in the run in period did not exhibit statistically significant responses in the context of the surface area reduction endpoint and the complete wound closure secondary endpoint.

FIG. 4 shows that the patient subpopulation that met the −15% to +30% wound size change criteria exhibited statistically significant (P<0.05) responses in the context of the surface area reduction endpoint and the complete wound closure secondary endpoint.

DETAILED DESCRIPTION

Figure 1A:
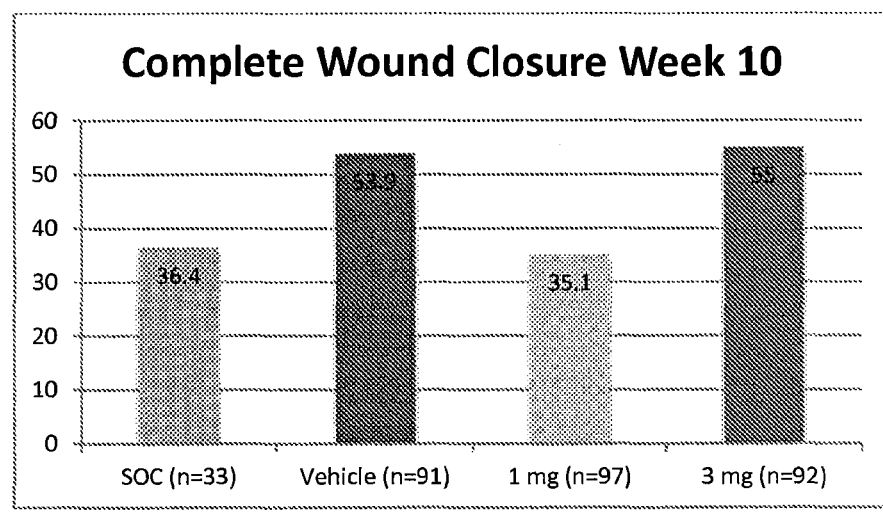

Wounds that do not heal at expected rates, including slow-healing wounds, delayed-healing wounds, incompletely healing wounds, dehiscent wounds, and chronic wounds, often result in infection and can lead to amputation or death. Cell-cell communication through the gap junctions plays pivotal roles in wound healing. It has been discovered that use of certain compounds, namely anti-connexin agents, including those described or referenced herein or otherwise now known or later developed, can block, inhibit, or alter cell communication to promote closure and healing in wounds that do not heal at expected rates, including slow-healing wounds, delayed-healing wounds, incompletely healing wounds, dehiscent wounds, and chronic wounds. Furthermore, as described herein, it has surprisingly and unexpectedly been discovered that healing of refractory chronic wounds by administration of one or more anti-connexin agents to connexin 26 (Cx26), connexin 30 (Cx30) or connexin 43 (Cx43), for example, can be further promoted by administering a desired anti-connexin agents to a patient whose chronic wound(s) remain within a certain size range during a standard of care (pre-treatment) run-in phase. Other connexin targets include connexin 30.3 (Cx30.3), connexin 31 (Cx31), connexin 31.1 (Cx31.1), connexin 32

(Cx32), connexin 37 (Cx37), connexin 40 (Cx40), and connexin 45 (Cx45), i.e., is an anti-connexin 26, 30, 30.3, 31, 31.1, 32, 37, 40, 43, or 45 polynucleotide. Preferably, during a pretreatment phase of from about 1 to about 30 days, preferably from about 5 days to about 20 days, even more preferably from about 7 days to about 14 days, the wound to be treated does not increase in size by more than about 30%, for example, or increase in size by more than about 35% as another example, or increase in size by more than about 30% or decrease in size by more than about 15%, for example.

It has been surprisingly observed that the refractory wounds that do not increase in wound size by about 30% or decrease in wound size by 15% are susceptible to administration of pharmaceutical compositions comprising from about 0.5 mg/mL to about 40 mg/mL, or from about 1 to 30 mg/mL anti-connexin polynucleotide at or in proximity to the wound a pharmaceutical composition comprising and a pharmaceutically acceptable carrier suitable for topical administration. In other embodiments, refractory wounds are chronic wounds, or wounds that do not heal at expected rates, such as delayed-healing wounds and incompletely healing wounds, which do not decrease in size by more than about 30% (+30%) over a standard-of-care treatment period using, for example, compression bandaging or off-loading devices over about two to four weeks. In still other embodiments, refractory wounds are chronic wounds, or wounds that do not heal at expected rates, such as delayed-healing wounds and incompletely healing wounds, which do not decrease in size by more than about 35% (+35%) over a standard-of-care treatment period using, for example, compression bandaging or off-loading devices, which do not increase in wound size by more than 15% (−15%). In further embodiments, refractory wounds are chronic wounds, or wounds that do not heal at expected rates, such as delayed-healing wounds and incompletely healing wounds, which do not increase or decrease in size by more than about −5%/+30%, −10%/+30%, −15%/+30%, −20%/+30%, 25%/+30% or −30%/+30%, over a standard-of-care treatment period using, for example, compression bandaging or off-loading devices, over about two to four weeks. In other embodiments, the standard of care treatment during the run-in period is reduction of pressure, or offloading. Foot pressures, shock, and shear may be reduced with appropriately fitted shoes, insoles, and socks. Total non-weight bearing using a wheelchair or crutches is another effective method of relieving pressure. Other off-loading standard of care modalities include total contact casts, removal casts, and removable cast walkers.

In some embodiments, a therapeutically effective amount of a composition of the invention comprises a pharmaceutically acceptable carrier and an anti-connexin agent such as a single-stranded anti-connexin 43 oligodeoxynucleotide present at a concentration from about 0.5 to about 40.0 mg per milliliter (mL; mg/mL) or from about 3 to about 30 mg/mL. Preferred concentrations range from about 1.5 to about 30 milligrams per milliliter (mg/mL), about 1.5 to about 10 mg/mL, or about 3, about 5, about 10, or about 30 mg/ml. In some aspects the total dose of anti-connexin polynucleotide administered may be about 100 µg to about 30 mg.

Particularly preferred concentrations for connexin antisense polynucleotides (e.g., single-stranded anti-connexin 43 oligodeoxynucleotides) range from about 150 µM to about 10,000 µM. Viewed another way, a refractory chronic skin wound can be effectively treated in accordance with the invention by administering about 150 µg to about 10,000 µg of a connexin antisense polynucleotide (e.g., a single-stranded anti-connexin 43 oligodeoxynucleotide) per square centimeter of wound surface area.

Definitions

As used herein, a "disorder" is any disorder, disease, or condition that would benefit from an agent that promotes healing of chronic or delayed healing wounds which are refractory to standard of care treatment, and/or reduces scar formation when such wounds are treated. For example, included are wound-associated abnormalities in connection with neuropathic, ischemic, and microvascular pathology; pressure over bony area [tailbone (sacral), hip (trochanteric), buttocks (ischial), or heel of the foot]; reperfusion injury; and conditions associated with valve reflux etiology and related conditions.

As used herein, "subject" refers to any mammal, including humans, domestic and farm animals, and zoo, sports, or pet animals, such as dogs, horses, cats, sheep, pigs, cows, etc. The preferred mammal herein is a human, including adults, children, and the elderly.

As used herein, "preventing" means preventing in whole or in part, or ameliorating or controlling.

As used herein, a "therapeutically effective amount" in reference to the compounds or compositions of the instant invention refers to the amount sufficient to induce a desired biological, pharmaceutical, or therapeutic result. That result can be alleviation of the signs, symptoms, or causes of a disease or disorder or condition, or any other desired alteration of a biological system. In the present invention, the result will involve the promotion and/or improvement of wound healing, including rates of wound healing and closure of wounds, in whole or in part. Other benefits include decreases in swelling, inflammation and/or scar formation, in whole or in part.

As used herein, the term "treating" refers to both therapeutic treatment and prophylactic or preventative measures.

As used herein, "simultaneously" is used to mean that the one or more anti-connexin agents (e.g., an anti-connexin polynucleotide, e.g., an antisense polynucleotide) are administered concurrently, whereas the term "in combination" is used to mean they are administered, if not simultaneously or in physical combination, then "sequentially" within a timeframe that they both are available to act therapeutically. Thus, administration "sequentially" may permit one agent to be administered within minutes (for example, 1, 2, 3, 4, 5, 10, 15, 20, 25, 30) minutes or a matter of hours, days, weeks or months after the other provided that one or more anti-connexin polynucleotides are concurrently present in effective amounts. The time delay between administration of the components will vary depending on the exact nature of the components, the interaction therebetween, and their respective half-lives.

As used herein, an "anti-connexin agent" decreases or inhibits expression of a connexin mRNA, pre-mRNA, and/or connexin protein. Anti-connexin agents include anti-connexin polynucleotides include, without limitation, antisense compounds such as antisense polynucleotides, other polynucleotides (such as polynucleotides having siRNA or ribozyme functions), peptidomimetics, and other compounds that interfere with connexin protein activity, function, transport, localization, etc. Suitable examples of an anti-connexin polynucleotide include an antisense polynucleotide that targets a connexin mRNA. Accordingly, suitable anti-connexin polynucleotides include, for example, antisense polynucleotides (e.g., Cx43 antisense polynucleotides) that modulate expression or activity of connexins and gap junctions in selected tissues, cells, and subjects.

The term "wound dressing" refers to a dressing for topical application to a wound and excludes compositions suitable for systemic administration. For example, the one or more anti-connexin agents (such as an anticonnexin polynucleotide) may be dispersed in or on a solid sheet of wound contacting material such as a woven or nonwoven textile material, or may be dispersed in a layer of foam such as polyurethane foam, or in a hydrogel such as a polyurethane hydrogel, a polyacrylate hydrogel, gelatin, carboxymethyl cellulose, pectin, alginate, and/or hyaluronic acid hydrogel, for example in a gel or ointment. In certain embodiments the one or more anti-connexin agents are dispersed in or on a biodegradable sheet material that provides sustained release of the active ingredients into the wound, for example a sheet of freeze-dried collagen, freeze-dried collagen/alginate mixtures (available under the Registered Trade Mark FIBRACOL from Johnson & Johnson Medical Limited) or freeze-dried collagen/oxidized regenerated cellulose (available under the Registered Trade Mark PROMOGRAN from Johnson & Johnson Medical Limited).

As used herein, "wound promoting matrix" includes for example, synthetic or naturally occurring matrices such as collagen, acellular matrix, crosslinked biological scaffold molecules, tissue based bioengineered structural framework, biomanufactured bioprostheses, and other implanted structures such as for example, vascular grafts suitable for cell infiltration and proliferation useful in the promotion of wound healing. Additional suitable biomatrix material may include chemically modified collagenous tissue to reduces antigenicity and immunogenicity. Other suitable examples include collagen sheets for wound dressings, antigen-free or antigen reduced acellular matrix (Wilson, et al. (1990), Trans Am Soc Artif Intern 36:340-343), or other biomatrices that have been engineered to reduce the antigenic response to the xenograft material. Other matrices useful in promotion of wound healing may include for example, processed bovine pericardium proteins comprising insoluble collagen and elastin (Courtman, et al. (1994), J Biomed Mater Res 28:655-666) and other acellular tissue which may be useful for providing a natural microenvironment for host cell migration to accelerate tissue regeneration (Malone J M et al. (1984) J Vasc Surg 1:181-91). The invention contemplates a synthetic or natural matrix comprising one or more anti-connexin agents described herein.

As used herein, the term "wound" includes an injury to any tissue, including for example, delayed or difficult to heal wounds, and chronic wounds. Examples of wounds may include both open and closed wounds. The term "wound" may also include for example, injuries to the skin and subcutaneous tissue initiated in different ways (e.g., pressure sores from extended bed rest and wounds induced by trauma) and with varying characteristics. Wounds may be classified into one of four grades depending on the depth of the wound: i) Grade I wounds limited to the epithelium; ii) Grade II wounds extending into the dermis; iii) Grade III wounds extending into the subcutaneous tissue; and iv) Grade IV (or full-thickness wounds) wounds wherein bones are exposed (e.g., a bony pressure point such as the greater trochanter or the sacrum).

The term "partial thickness wound" refers to wounds that encompass Grades I-III. Examples of partial thickness wounds include pressure sores, venous stasis ulcers, and diabetic ulcers. The present invention contemplates treating all wounds of a type that do not heal at expected rates, including, delayed-healing wounds, incompletely healing wounds, and chronic wounds.

"Wound that does not heal at the/an expected rate" means an injury to any tissue, including delayed or difficult to heal wounds (including delayed or incompletely healing wounds), and chronic wounds. Examples of wounds that do not heal at the expected rate include ulcers, such as diabetic ulcers, diabetic foot ulcers, vasculitic ulcers, arterial ulcers, venous ulcers, venous stasis ulcers, pressure ulcers, decubitus ulcers, infectious ulcers, trauma-induced ulcers, burn ulcers, ulcerations associated with pyoderma gangrenosum, and mixed ulcers. Other wounds that do not heal at expected rates include dehiscent wounds.

As used herein, a "delayed" or "difficult to heal" wound may include, for example, a wound that is characterized at least in part by 1) a prolonged inflammatory phase, 2) a slow forming extracellular matrix, and/or 3) a decreased rate of epithelialization or closure.

The term "chronic wound" generally refers to a wound that has not healed. Wounds that do not heal within three months, for example, are considered chronic. Chronic wounds include venous ulcers, venous stasis ulcers, arterial ulcers, pressure ulcers, diabetic ulcers, diabetic foot ulcers, vasculitic ulcers, decubitus ulcers, burn ulcers, trauma-induced ulcers, infectious ulcers, mixed ulcers, and pyoderma gangrenosum. The chronic wound may be an arterial ulcer that comprises ulcerations resulting from complete or partial arterial blockage. The chronic wound may be a venous or venous stasis ulcer that comprises ulcerations resulting from a malfunction of the venous valve and the associated vascular disease. In certain embodiments a method of treating a chronic wound is provided where the chronic wound is characterized by one or more of the following AHCPR stages of pressure ulceration: stage 1, stage 2, stage 3, and/or stage 4.

As used herein, chronic wound may refer to, for example, a wound that is characterized at least in part by one or more of (1) a chronic self-perpetuating state of wound inflammation, (2) a deficient and defective wound extracellular matrix, (3) poorly responding (senescent) wound cells especially fibroblasts, limiting extracellular matrix production, and/or (4) failure of re-epithelialization due in part to lack of the necessary extracellular matrixorchestration and lack of scaffold for migration. Chronic wounds may also be characterized by 1) prolonged inflammation and proteolytic activity leading to ulcerative lesions, including for example, diabetic, pressure (decubitous), venous, and arterial ulcers; 2) progressive deposition of matrix in the affected area, 3) longer repair times, 4) less wound contraction, 5) slower re-epithelialization, and 6) increased thickness of granulation tissue.

The term "refractory" chronic wound or "refractory" wound refers to wounds that do not heal at expected rates, such as delayed-healing wounds, incompletely healing wounds, and chronic wounds, and which do not, for example, increase in wound size by more than about 30% (are partially refractory to administration of standard of care) and which do not decrease in wound size by more than 15% (−15%) (are totally refractory to administration of standard of care) during a two to four week run-in period. Following presentation for treatment of a wound that does not heal at the expected rate, the wound is pre-treated using standard of care treatment using, for example, compression bandaging or off-loading devices. In some embodiments the refractory wounds are wounds that do not heal at expected rates and which do not increase in wound size by more than about 30% and do not decrease in size by more than about 20%, 25%, 30%, or 35% during the run-in period. In other embodiments, refractory wounds are chronic wounds, or wounds that do not heal at expected rates, such as delayed-healing wounds and incompletely healing wounds, which do not decrease in size by more than about 30% (+30%) over a standard-of-care treatment period using, for example, compression bandaging or off-loading devices, over about two to four weeks. In still other embodiments, refractory wounds are chronic wounds, or wounds that do not heal at expected rates, such as delayed-healing wounds and incompletely healing wounds, which do not decrease in size by more than about 35% (+35%) over a standard-of-care treatment period using, for example, compression bandaging or off-loading devices, which do not increase in wound size by more than 15% (−15%). In further embodiments, refractory wounds are chronic wounds, or wounds that do not heal at expected rates, such as delayed-healing wounds and incompletely healing wounds, which do not increase or decrease in size by more than about −5%/+30%, −10%/+30%, −15%/+30%, −20%/+30%, 25%/+30% or −30%/+30%, over a standard-of-care treatment period using, for example, compression bandaging or off-loading devices, over about two to four weeks. In some aspects of this disclosure, the refractory wound may be, for example, a refractory skin ulcer, such as a venous leg ulcer, or diabetic foot ulcer. In yet another aspect, the invention includes methods for treating a subject having or suspected of having any diseases, disorders, and/or conditions characterized in whole or in part by a chronic wound or delayed or incomplete wound healing, or other wound that does not heal at an expected rate. In some embodiments, the patient has a diabetic ulcer, a diabetic foot ulcer, a vasculitic ulcer, a venous ulcer, a venous stasis ulcer, an arterial ulcer, a pressure ulcer, a decubitus ulcer, an infectious ulcer, a trauma-induced ulcer, a burn ulcer, ulcerations associated with pyoderma gangrenosum, or a mixed ulcer or ulcers.

In the context of the instant inventions, the anti-connexin agents are preferably administered topically (at and/or around the site to be treated). Suitably, the anti-connexin agents, e.g., anti-connexin antisense polynucleotides are combined with a pharmaceutically acceptable carrier, vehicle or diluent to provide a pharmaceutical composition.

Exemplary chronic wounds may include "pressure ulcers." Exemplary pressure ulcers may be classified into 4 stages based on AHCPR (Agency for Health Care Policy and Research, U.S. Department of Health and Human Services) guidelines. A stage I pressure ulcer is an observable pressure related alteration of intact skin whose indicators as compared to the adjacent or opposite area on the body may include changes in one or more of the following: skin temperature (warmth or coolness), tissue consistency (firm or boggy feel) and/or sensation (pain, itching). The ulcer appears as a defined area of persistent redness in lightly pigmented skin, whereas in darker skin tones, the ulcer may appear with persistent red, blue, or purple hues. Stage 1 ulceration may include nonblanchable erythema of intact skin and the heralding lesion of skin ulceration. In individuals with darker skin, discoloration of the skin, warmth, edema, induration, or hardness may also be indicators of stage 1 ulceration. Stage 2 ulceration may be characterized by partial thickness skin loss involving epidermis, dermis, or both. The ulcer is superficial and presents clinically as an abrasion, blister, or shallow crater. Stage 3 ulceration may be characterized by full thickness skin loss involving damage to or necrosis of subcutaneous tissue that may extend down to, but not through, underlying fascia. The ulcer presents clinically as a deep crater with or without undermining of adjacent tissue. Stage 4 ulceration may be characterized by full thickness skin loss with extensive destruction, tissue necrosis, or damage to muscle, bone, or supporting structures (e.g., tendon, joint capsule). In certain embodiments a method of treating a chronic wound is provided where the chronic wound is characterized by one or more of the following AHCPR stages of pressure ulceration: stage 1, stage 2, stage 3, and/or stage 4.

Exemplary chronic wounds may also include "decubitus ulcers." Exemplary decubitus ulcers may arise as a result of prolonged and unrelieved pressure over a bony prominence that leads to ischemia. The wound tends to occur in patients who are unable to reposition themselves to off-load weight, such as paralyzed, unconscious, or severely debilitated persons. As defined by the U.S. Department of Health and Human Services, the major preventive measures include identification of high-risk patients; frequent assessment; and prophylactic measures such as scheduled repositioning, appropriate pressure-relief bedding, moisture barriers, and adequate nutritional status. Treatment options may include for example, pressure relief, surgical and enzymatic debridement, moist wound care, and control of the bacterial load. In certain embodiments a method of treating a chronic wound is provided wherein the chronic wound is characterized by decubitus ulcer or ulceration, which results from prolonged, unrelieved pressure over a bony prominence that leads to ischemia.

Chronic wounds may also include "arterial ulcers." Chronic arterial ulcers are generally understood to be ulcerations that accompany arteriosclerotic and hypertensive cardiovascular disease. They are painful, sharply marginated, and often found on the lateral lower extremities and toes. Arterial ulcers may be characterized by complete or partial arterial blockage, which may lead to tissue necrosis and/or ulceration. Signs of arterial ulcer may include, for example, pulselessness of the extremity; painful ulceration; small, punctate ulcers that are usually well circumscribed; cool or cold skin; delayed capillary return time (briefly push on the end of the toe and release, normal color should return to the toe in about 3 seconds or less); atrophic appearing skin (for example, shiny, thin, dry); and loss of digital and pedal hair. In certain embodiments a method of treating a chronic wound is provided wherein the chronic wound is characterized by arterial ulcers or ulcerations due to complete or partial arterial blockage.

Exemplary chronic wounds may include "venous ulcers." Exemplary venous ulcers are the most common type of ulcer affecting the lower extremities and may be characterized by malfunction of the venous valve. The normal vein has valves that prevent the backflow of blood. When these valves become incompetent, the backflow of venous blood causes venous congestion. Hemoglobin from the red blood cells escapes and leaks into the extravascular space, causing the brownish discoloration commonly noted. It has been shown that the transcutaneous oxygen pressure of the skin surrounding a venous ulcer is decreased, suggesting that there are forces obstructing the normal vascularity of the area. Lymphatic drainage and flow also plays a role in these ulcers. The venous ulcer may appear near the medial malleolus and usually occurs in combination with an edematous and indurated lower extremity; it may be shallow, not too painful and may present with a weeping discharge from the affected site. In certain embodiments a method of treating a chronic wound is provided wherein the chronic wound is characterized by venous ulcers or ulcerations due to malfunction of the venous valve and the associated vascular disease. In certain embodiments a method of treating a chronic wound is provided wherein the chronic wound is characterized by arterial ulcers or ulcerations due to complete or partial arterial blockage.

Exemplary chronic wounds may include "venous stasis ulcers." Stasis ulcers are lesions associated with venous insufficiency are more commonly present over the medial malleolus, usually with pitting edema, varicosities, mottled pigmentation, erythema, and nonpalpable petechiae and purpura. The stasis dermatitis and ulcers are generally pruritic rather than painful. Exemplary venous stasis ulcers may be characterized by chronic passive venous congestion of the lower extremities results in local hypoxia. One possible mechanism of pathogenesis of these wounds includes the impediment of oxygen diffusion into the tissue across thick perivascular fibrin cuffs. Another mechanism is that macromolecules leaking into the perivascular tissue trap growth factors needed for the maintenance of skin integrity. Additionally, the flow of large white blood cells slows due to venous congestion, occluding capillaries, becoming activated, and damaging the vascular endothelium to predispose to ulcer formation. In certain embodiments a method of treating a chronic wound is provided wherein the chronic wound is characterized by venous ulcers or ulcerations due to malfunction of the venous valve and the associated vascular disease. In certain embodiments a method of treating a chronic wound is provided wherein the chronic wound is characterized by venous stasis ulcers or ulcerations due to chronic passive venous congestion of the lower extremities and/or the resulting local hypoxia.

Exemplary chronic wounds may include "diabetic ulcers." Diabetic patients are prone to ulcerations, including foot ulcerations, due to both neurologic and vascular complications. Peripheral neuropathy can cause altered or complete loss of sensation in the foot and/or leg. Diabetic patients with advanced neuropathy lose all ability for sharp-dull discrimination. Any cuts or trauma to the foot may go completely unnoticed for days or weeks in a patient with neuropathy. It is not uncommon to have a patient with neuropathy notice that the ulcer "just appeared" when, in fact, the ulcer has been present for quite some time. For patients of neuropathy, strict glucose control has been shown to slow the progression of the disease. Charcot foot deformity may also occur as a result of decreased sensation. People with "normal" feeling in their feet have the ability to sense automatically when too much pressure is being placed on an area of the foot. Once identified, our bodies instinctively shift position to relieve this stress. A patient with advanced neuropathy loses this ability to sense the sustained pressure insult, as a result, tissue ischemia and necrosis may occur leading to for example, plantar ulcerations. Additionally, microfractures in the bones of the foot, if unnoticed and untreated, may result in disfigurement, chronic swelling and additional bony prominences. Microvascular disease is one of the significant complications for diabetics, which may also lead to ulcerations. In certain embodiments a method of treating a chronic wound is provided wherein the chronic wound is characterized by diabetic foot ulcers and/or ulcerations due to both neurologic and vascular complications of diabetes.

Exemplary chronic wounds can include "traumatic ulcers." Formation of traumatic ulcers may occur as a result of traumatic injuries to the body. These injuries include, for example, compromises to the arterial, venous or lymphatic systems; changes to the bony architecture of the skeleton; loss of tissue layers-epidermis, dermis, subcutaneous soft tissue, muscle or bone; damage to body parts or organs and loss of body parts or organs. In certain embodiments, a method of treating a chronic wound is provided wherein the chronic wound is characterized by ulcerations associated with traumatic injuries to the body.

Exemplary chronic wounds can include "burn ulcers", including first degree burn (i.e. superficial, reddened area of skin); second degree burn (a blistered injury site which may heal spontaneously after the blister fluid has been removed); third degree burn (burn through the entire skin and usually require surgical intervention for wound healing); scalding (may occur from scalding hot water, grease or radiator fluid); thermal (may occur from flames, usually deep burns); chemical (may come from acid and alkali, usually deep burns); electrical (either low voltage around a house or high voltage at work); explosion flash (usually superficial injuries); and contact burns (usually deep and may occur from muffler tail pipes, hot irons and stoves). In certain embodiments, a method of treating a chronic wound is provided wherein the chronic wound is characterized by ulcerations associated with burn injuries to the body.

Exemplary chronic wounds can include "vasculitic ulcers." Vasculitic ulcers also occur on the lower extremities and are painful, sharply marginated lesions, which may have associated palpable purpuras and hemorrhagic bullae. The collagen diseases, septicemias, and a variety of hematological disorders (e.g., thrombocytopenia, dysproteinemia) may be the cause of this severe, acute condition.

Exemplary chronic wounds can include pyoderma gangrenosum. Pyoderma gangrenosum occurs as single or multiple, very tender ulcers of the lower legs. A deep red to purple, undermined border surrounds the purulent central defect. Biopsy typically fails to reveal a vasculitis. In half the patients it is associated with a systemic disease such as ulcerative colitis, regional ileitis, or leukemia. In certain embodiments, a method of treating a chronic wound is provided wherein the chronic wound is characterized by ulcerations associated with pyoderma gangrenosum.

Exemplary chronic wounds can include infectious ulcers. Infectious ulcers follow direct innoculation with a variety of organisms and may be associated with significant regional adenopathy. Mycobacteria infection, anthrax, diphtheria, blastomyosis, sporotrichosis, tularemia, and cat-scratch fever are examples. The genital ulcers of primary syphilis are typically nontender with a clean, firm base. Those of chancroid and granuloma inguinale tend to be ragged, dirty, and more extravagant lesions. In certain embodiments, a method of treating a chronic wound is provided wherein the chronic wound is characterized by ulcerations associated with infection.

As used herein, the term "dehiscent wound" refers to a wound, usually a surgical wound, which has ruptured or split open. In certain embodiments, a method of treating a wound that does not heal at the expected rate is provided wherein the wound is characterized by dehiscence.

Anti-Connexin Agents
Anti-Connexin Polynucleotides

Anti-connexin polynucleotides include connexin antisense polynucleotides as well as polynucleotides which have functionalities that enable them to downregulate connexin expression (for example, by downregulation of mRNA transcription or translation). In the case of downregulation, this has the effect of reducing direct cell-cell communication by gap junctions at the site at which connexin expression is down-regulated.

The inventions generally relate to the use of an anti-connexin agent, preferably an anti-connexin polynucleotide, including, for example, an anti-connexin oligodeoxynucleotide (ODN), directed to a messenger RNA (mRNA) or precursor thereof that codes a connexin protein. Representative anti-connexin polynucleotides used in the methods and articles of manufacture of this disclosure include connexin antisense polynucleotides, as well as RNAi polynucleotides, siRNA polynucleotides, shRNA polynucleotides, ribozymes, DNAzymes, and other anti-connexin polynucleotides that target a connexin messenger RNA (mRNA) or precursor thereof. Other anti-connexin agents within the scope of the invention include peptidomimetics and connexin phosphorylation agents.

In the context of anti-connexin polynucleotides, such molecules are preferably single-stranded polynucleotides, although under physiological conditions all or portions of such molecules may include one or more partially or completely double-stranded regions. Such polynucleotides include those having modified and/or unmodified backbone, and can be produced recombinantly or synthetic chemistry.

In another embodiment, the anti-connexin polynucleotide may be an anti-connexin 43, anti-connexin 26 and anti-connexin 30 polynucleotides, for example, an ODN, such as a single-stranded anti-connexin oligodeoxynucleotide to connexin 26, connexin 30 or connexin 43. In some embodiments the anti-connexin polynucleotide is an anti-connexin 43 polynucleotide. In one embodiment, the anti-connexin polynucleotide is a connexin 43 antisense oligodeooxy-nucleotide such as a single-stranded anti-connexin oligodeoxynucleotide to connexin.

In certain other embodiments, the anti-connexin agent is an anti-connexin polynucleotide that targets a connexin mRNA or precursor thereof (i.e., pre-mRNA), particularly an mRNA or pre-mRNA that codes for connexin 43 (Cx43), connexin 26 (Cx26), connexin 37 (Cx37), connexin 30 (Cx30), connexin 30.3 (Cx30.3), connexin 31 (Cx31), connexin 31.1 (Cx31.1), or connexin 32 (Cx32), connexin 40 (Cx40), and connexin 45 (Cx45), i.e., is an anti-connexin 43, 26, 37, 30, 30.3, 31, 31.1, 32, 40 or 45 polynucleotide.

Particularly preferred anti-connexin polynucleotides include anti-connexin oligodeoxynucleotides such as anti-connexin 43 oligodeoxynucleotides. Preferred anti-connexin polynucleotides contain from about 18 to about 32 polynucleotides.

Accordingly, in another aspect, the invention provides formulations comprising at least one anti-connexin agent, e.g., a connexin antisense polynucleotide, together with a pharmaceutically acceptable carrier or vehicle. In one preferred form, such formulations contain a connexin antisense polynucleotide that targets a single connexin mRNA species, most preferably, connexin 43 mRNA or pre-mRNA. Alternatively, the formulation can contain an anti-connexin agent, e.g., a connexin antisense polynucleotide, that targets more than one connexin mRNA species, e.g., an mRNA species that codes for Cx43 as well as an mRNA species that codes for Cx30, Cx26, Cx37, Cx31.1, or Cx32 and others as noted herein.

According to one aspect, the downregulation of connexin expression may be based generally upon the antisense approach using antisense polynucleotides (such as DNA or RNA polynucleotides), and more particularly upon the use of antisense oligodeoxynucleotides (ODN). These polynucleotides (e.g., ODN) target the connexin protein (s) to be down-regulated. Typically the polynucleotides are single stranded, but may be double stranded.

The antisense polynucleotide may inhibit transcription and/or translation of a connexin. Preferably the polynucleotide is a specific inhibitor of transcription and/or translation from the connexin gene or mRNA, and does not inhibit transcription and/or translation from other genes or mRNAs.

The product may bind to the connexin gene or mRNA either (i) 5' to the coding sequence, and/or (ii) to the coding sequence, and/or (iii) 3' to the coding sequence.

The antisense polynucleotide is generally antisense to a connexin mRNA. Such a polynucleotide may be capable of hybridizing to the connexin mRNA and may thus inhibit the expression of connexin by interfering with one or more aspects of connexin mRNA metabolism including transcription, mRNA processing, mRNA transport from the nucleus, translation or mRNA degradation. The antisense polynucleotide typically hybridizes to the connexin mRNA to form a duplex which can cause direct inhibition of translation and/or destabilization of the mRNA. Such a duplex may be susceptible to degradation by nucleases.

The antisense polynucleotide may hybridize to all or part of the connexin mRNA. Typically the antisense polynucleotide hybridizes to the ribosome binding region or the coding region of the connexin mRNA. The polynucleotide may be complementary to all of or a region of the connexin mRNA. For example, the polynucleotide may be the exact complement of all or a part of connexin mRNA. However, absolute complementarity is not required and polynucleotides which have sufficient complementarity to form a duplex having a melting temperature of greater than about 20° C., 30° C., or 40° C. under physiological conditions are particularly suitable for use in the present invention.

Thus the polynucleotide is typically a homologue of a sequence complementary to the mRNA. The polynucleotide may be a polynucleotide which hybridizes to the connexin mRNA under conditions of medium to high stringency such as 0.03M sodium chloride and 0.03M sodium citrate at from about 50° C. to about 60° C.

For certain aspects, suitable polynucleotides are typically from about 6 to 40 nucleotides in length. Preferably a polynucleotide may be from about 12 to about 35 nucleotides in length, or alternatively from about 12 to about 20 nucleotides in length or more preferably from about 18 to about 32 nucleotides in length. According to an alternative aspect, the polynucleotide may be at least 40 nucleotides in length.

The inventions include pharmaceutical compositions comprising (a) a therapeutically effect amount of a pharmaceutically acceptable anti-connexin agent (e.g., an anti-connexin 43 oligodeoxynucleotide) and (b) a pharmaceutically acceptable carrier or diluent. Therapeutically effective doses and dose concentrations are described herein. In some embodiments, the compositions or treatment regimens of the invention include compositions that include multiple anti-connexin agent species (e.g., two or more anti-connexin polynucleotide species wherein each species targets a different connexin mRNA or pre-mRNA species; an anti-connexin polynucleotide that can target two or more different connexin mRNA or pre-mRNA species because of conserved sequence identity over at least a portion of the different connexin mRNA or pre-mRNA species targeted by the anti-connexin polynucleotide; etc.).

The anti-connexin agents of this invention may include those agents or compounds capable of inducing phosphorylation on connexin amino acid residues in order to induce gap junction or hemichannel closure. Exemplary sites of phosphorylation include one or more of a tyrosine, serine or threonine residues on the connexin protein. In certain embodiments, modulation of phosphorylation may occur on one or more residues on one or more connexin proteins. Exemplary gap junction phosphorylating agents are well known in the art and may include, for example, c-Src tyrosine kinase or other G protein-coupled receptor agonists.

See Giepmans B, J. Biol. Chem., Vol. 276, Issue 11, 8544-8549, Mar. 16, 2001. In one embodiment, modulation of phosphorylation on one or more of these residues impacts hemichannel function, particularly by closing the hemichannel. In another embodiment, modulation of phosphorylation on one or more of these residues impacts gap junction function, particularly by closing the gap junction. Gap junction phosphorylating agents that target the closure of connexin 43 gap junctions and hemichannels are preferred.

Still other anti-connexin agents include connexin carboxy-terminal polypeptides. See Gourdie et al., WO2006/069181.

In certain another aspect, gap junction modifying agent may include, for example, aliphatic alcohols; octanol; heptanol; anesthetics (e.g. halothane), ethrane, fluothane, propofol and thiopental; anandamide; arylaminobenzoate (FFA: flufenamic acid and similar derivatives that are lipophilic); carbenoxolone; Chalcone: (2',5'-dihydroxychalcone); CHFs (Chlorohydroxyfuranones); CMCF (3-chloro-4-(chloromethyl)-5-hydroxy-2(5H)-furanone); dexamethasone; doxorubicin (and other anthraquinone derivatives); eicosanoid thromboxane A(2) (TXA(2)) mimetics; NO (nitric oxide); Fatty acids (e.g. arachidonic acid, oleic acid and lipoxygenase metabolites; Fenamates (flufenamic (FFA), niflumic (NFA) and meclofenamic acids (MFA)); Genistein; glycyrrhetinic acid (GA):18a-glycyrrhetinic acid and 18-beta-glycyrrhetinic acid, and derivatives thereof; lindane; lysophosphatidic acid; mefloquine; menadione; 2-Methyl-1,4-naphthoquinone, vitamin K(3); nafenopin; okadaic acid; oleamide; oleic acid; PH, gating by intracellular acidification; e.g., acidifying agents; polyunsaturated fatty acids; fatty acid GJIC inhibitors (e.g., oleic and arachidonic acids); quinidine; quinine; all trans-retinoic acid; and tamoxifen.

The anti-connexin agents of the invention, particularly anti-connexin polynucleotides such as connexin antisense polynucleotides (e.g., a connexin antisense oligodeooxynucleotide such as a single-stranded anti-connexin 43 oligodeoxynucleotide), can be used to effect treatment of a chronic skin wound by administering to such a wound a composition that comprises about 0.001 milligram (mg) to about 10, 1, 0.1, or 0.01 mg of the anti-connexin agent per kilogram (kg) body weight in a pharmaceutically acceptable carrier. Preferred amounts of the anti-connexin agent (e.g., a single-stranded anti-connexin 43 oligodeoxynucleotide) in such a composition include about 0.01 mg to about 10 mg per kg body weight (mg/kg), about 0.01 mg to about 10 mg/kg, and about 0.5 to about 1.0 mg/kg. The dosage may also be about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 52.5, 55.0, 57.5, 60.0, 62.5, 65.0, 67.5, 70.0, 72.5, 75.0, 77.5, 80.0, 82.5, 85.0, 87.5, 90.0, 92.5, 95.0, 97.5, or about 100.0 mg per kg body weight, or any range or subrange between any two of the recited doses, or any dose falling within the range of from about 0.1 to about 100 mg per kg body weight.

In some embodiments, one or more doses of the pharmaceutical composition may be administered at appropriate intervals. In some aspects, the total dose (weight) of anti-connexin polynucleotide administered to the refractory wound may be about 100 µg to about 1 mg. In some aspects, the total dose (w) of anti-connexin polynucleotide administered may 100 µg, 200 µg, 300 µg, 400 µg, 500 µg, 600 µg, 700 µg, 800 µg, 900 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, or about 30 mg, or any amount ranging between any two of those doses. In other embodiments, the doses will be about 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 52.5, 55.0, 57.5, 60.0, 62.5, 65.0, 67.5, 70.0, 72.5, 75.0, 77.5, 80.0, 82.5, 85.0, 87.5, 90.0, 92.5, 95.0, 97.5, 100.0, 105, 110, 115, 120, 125, 130, 135, 140, 145, 150, 155, 160, 65, 170, 175, 180, 185, 190, 195, 200, 210, 220, 230, 250, 260, 270, 280, 290, 300, 310, 320, 330, 340, 350, 360, 370, 380, 390, 400, 410, 420, 430, 440, 450, 460, 470, 480, 490, or about 500 milligrams per square centimeter, or any range or subrange between any two of the recited doses, or any dose falling within the range of about 1.0 to about 500 milligrams per square centimeter.

In some aspects the dose of anti-connexin polynucleotide is administered in a volume of about 25 ul to about 3 ml. Preferred dose volumes for compositions that include a pharmaceutically acceptable carrier and from 0.5 to about 1.0 mg of an anti-connexin agent (e.g., a single-stranded anti-connexin 43 oligodeoxynucleotide) range from about 25-100 microliter (µL), from about 100-200 µL, from about 200-500 µL, or from about 500-1000 µL.

In other embodiments, the anti-connexin agent is applied at about a 20 µM, 30 µM, 50 µM, 60 µM, 70 µM, 80 µM, 90 µM, 100 µM, 10-200 µM, 200-300 µM, 300-400 µM, 400-500 µM, 500-600 µM, 600-700 µM, 700-800 µM, 800-900 µM, 900-1000 or 1000-1500 µM, or 1500 µM-2000 µM, 2000 µM-3000 µM, 3000 µM-4000 µM, 4000 µM-5000 µM, 5000 µM-6000 µM, 6000 µM-7000 µM, 7000 µM-8000 µM, 8000 µM-9000 µM, 9000 µM-10,000 µM, 10,000 µM-11,000 µM, 11,000 µM-12,000 µM, 12,000 µM-13,000 µM, 13,000 µM-14,000 µM, 14,000 µM-15,000 µM, 15,000 µM-20,000 µM, 20,000 µM-30,000 µM, 30,000 µM-50,000 or greater, or any range or subrange between any two of the recited doses, or any dose falling within the range of from about 20 µM to about 50,000 µM.

The connexin protein or proteins targeted by the polynucleotide will be dependent upon the site at which downregulation is to be effected. This reflects the non-uniform make-up of gap junction(s) at different sites throughout the body in terms of connexin sub-unit composition. The connexin is a connexin that naturally occurs in a human or animal in one aspect or naturally occurs in the tissue in which connexin expression or activity is to be decreased. The connexin gene (including coding sequence) generally has homology or nucleotide sequence identity with the coding sequence of one or more of the specific connexins mentioned herein. The connexin is typically an α or β connexin. Preferably the connexin is an α connexin and is expressed in the tissue to be treated.

Some connexin proteins are, however, more ubiquitous than others in terms of distribution in tissue. One of the most widespread is connexin 43. Polynucleotides targeted to connexin 43 are particularly suitable for use in the present invention. In other aspects other connexins are targeted. In one preferred aspect, the antisense polynucleotides are targeted to the mRNA of one connexin protein only. Most preferably, this connexin protein is connexin 43. In another aspect, connexin protein is connexin Cx26, Cx30, Cx30.3, Cx31, Cx31.1, Cx32, Cx37, Cx40, or Cx45. In other aspects, the connexin protein is connexin 26 or 30.

It is also contemplated that polynucleotides targeted to separate connexin proteins be used in combination (for example 1, 2, 3, 4, or more different connexins may be targeted). For example, polynucleotides targeted to connexin 43, and one or more other members of the connexin family (such as connexin Cx26, Cx30, Cx30.3, Cx31, Cx31.1, Cx32, Cx37, Cx40, or Cx45 can be used in combination.

Alternatively, the anticonnexin polynucleotides may be part of compositions that may comprise polynucleotides to more than one connexin protein. Preferably, one of the connexin proteins to which polynucleotides are directed is connexin 43. Other connexin proteins to which oligthe polynucleotides are directed may include, for example, connexin Cx26, Cx30, Cx30.3, Cx31, Cx31.1, Cx32, Cx37, Cx40, or Cx45.

Individual anti-connexin agents may be specific to a particular connexin, or may target 1, 2, 3, or more different connexins. Specific polynucleotides will in some embodiments target sequences in the targeted connexin gene, mRNA, or pre-mRNA that are not conserved between connexins, whereas multi-specific polynucleotides will target conserved sequences for various connexins.

The polynucleotides for use in the invention may suitably be unmodified phosphodiester oligomers. Such oligodeoxynucleotides may vary in length. A 30-mer polynucleotide has been found to be particularly suitable.

Many aspects of the invention are described with reference to oligodeoxynucleotides. However, it is understood that other suitable polynucleotides (such as RNA polynucleotides) and anti-connexin agents may be used in these aspects.

The anticonnexin polynucleotides may be chemically modified. This may enhance their resistance to nucleases and may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. Alternatively, mixed backbone oligonucleotides ("MBOs") may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides. Methods of preparing modified backbone and mixed backbone oligonucleotides are known in the art.

The precise sequence of representative preferred antisense polynucleotides used in the invention will depend upon the target connexin protein. As described, suitable connexin antisense polynucleotides can include polynucleotides such as oligodeoxynucleotides.

Suitable polynucleotides for the preparation of the combined polynucleotide compositions described herein include for example, polynucleotides to connexin 43 and polynucleotides for connexins 26, 30, 31.1, 32, and 37.

Although the precise sequence of the anticonnexin polynucleotide used in the invention will depend upon the target connexin protein, for connexin 43, antisense polynucleotides having the following sequences have been found to be particularly suitable:

```
SEQ. ID. NO: 1:
5'-GTA ATT GCG GCA AGA AGA ATT GTT TCT GTC-3'

SEQ. ID. NO: 2:
5'-GTA ATT GCG GCA GGA GGA ATT GTT TCT GTC-3'

SEQ. ID. NO: 3:
5'-GGC AAG AGA CAC CAA AGA CAC TAC CAG CAT-3'

SEQ. ID. NO: 7:
5'-GAC AGA AAC AAT TCC TCC TGC CGC ATT TAC-3'
```

Suitable antisense polynucleotides for connexins 26, 31.1, and 32 have the following sequences:

```
SEQ. ID. NO: 4 (Cx26):
5'-TCC TGA GCA ATA CCT AAC GAA CAA ATA-3'

SEQ. ID. NO: 5 (Cx31.1):
5'-CGT CCG AGC CCA GAA AGA TGA GGT C-3'

SEQ. ID. NO: 6 (Cx32):
5'-TTT CTT TTC TAT GTG CTG TTG GTG A-3'
```

Polynucleotides, including ODN's, directed to connexin proteins can be selected in terms of their nucleotide sequence by any convenient, and conventional, approach. For example, the computer programs MacVector and OligoTech (from Oligos etc. Eugene, Oreg., USA) can be used. Once selected, the ODN's can be synthesized using a DNA synthesizer.

Polynucleotide Homologues

Homology, homologues, and nucleotide sequence identity are described herein (for example, the polynucleotide may be a homologue of a complement to a sequence in connexin mRNA). Such a polynucleotide typically has at least about 70% nucleotide sequence identity, preferably at least about 80%, at least about 90%, at least about 95%, at least about 97% or at least about 99% sequence identity with the relevant sequence, for example, over a region of at least about 15, at least about 20, at least about 40, at least about 100 more contiguous nucleotides (of the homologous sequence). Homology or sequence identity may be calculated based on any method in the art.

For example, the BLAST algorithm performs a statistical analysis of the similarity between two sequences; see, e.g., Karlin and Altschul (1993), Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to a second sequence is less than about 1, preferably less than about 0.1, more preferably less than about 0.01, and most preferably less than about 0.001.

The homologous sequence typically differs from the relevant sequence by at least about (or by no more than about) 2, 5, 10, 15, 20, or more mutations (which may be substitutions, deletions or insertions). These mutations may be measured across any of the regions mentioned above in relation to calculating sequence identity.

The homologous sequence typically hybridizes selectively to the original sequence at a level significantly above background. Selective hybridization is typically achieved using conditions of medium to high stringency (for example 0.03M sodium chloride and 0.03M sodium citrate at from about 50° C. to about 60° C.). However, such hybridization may be carried out under any suitable conditions known in the art (see Sambrook, et al. (1989), Molecular Cloning: A Laboratory Manual). For example, if high stringency is required, suitable conditions include 0.2×SSC at 60° C. If lower stringency is required, suitable conditions include 2×SSC at 60° C.

Dosage Forms and Formulations and Administration

The anti-connexin agents of the invention of the may be administered to a subject in need of treatment, such as a subject with any of the wounds mentioned herein. The condition of the subject can thus be improved. The anti-connexin agent may be used in the treatment of the subject's body by therapy. They may be used in the manufacture of a medicament to treat any of the wounds mentioned herein.

The anti-connexin agent (e.g., an anti-connexin polynucleotide) may be present in a substantially isolated form. It will be understood that the product may be mixed with carriers or diluents that will not interfere with the intended purpose of the product and still be regarded as substantially isolated. A product of the invention may also be in a substantially purified form, in which case it will generally comprise about 80%, 85%, or 90%, including, for example, at least about 95%, at least about 98% or at least about 99% of the polynucleotide or dry mass of the preparation.

Depending on the intended route of administration, the pharmaceutical products, pharmaceutical compositions, combined preparations and medicaments of the invention may, for example, take the form of solutions, suspensions, instillations, sprays, salves, creams, gels, foams, ointments, emulsions, lotions, paints, sustained release formulations, or powders, and typically contain about 0.01% to about 1% of active ingredient(s), about 1%-50% or active ingredient(s), about 2%-60% of active ingredient(s), about 2%-70% of active ingredient(s), or up to about 90% of active ingredient(s). Other suitable formulations include pluronic gel-based formulations, carboxymethylcellulose(CMC)-based formulations, and hyroxypropylmethylcellulose(HPMC)-based formulations. Other useful formulations include slow or delayed release preparations.

Gels or jellies may be produced using a suitable gelling agent including, but not limited to, gelatin, tragacanth, or a cellulose derivative and may include glycerol as a humectant, emollient, and preservative. Ointments are semi-solid preparations that consist of the active ingredient incorporated into a fatty, waxy, or synthetic base. Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Preferably the anti-connexin agents useful in practicing the instant inventions are combined with a pharmaceutically acceptable carrier or diluent to produce a pharmaceutical composition. Suitable carriers and diluents include isotonic saline solutions, for example phosphate-buffered saline. Suitable diluents and excipients also include, for example, saline, dextrose, glycerol, or the like, and combinations thereof. In addition, if desired substances such as wetting or emulsifying agents, stabilizing or ph buffering agents may also be present.

The term "pharmaceutically acceptable carrier" refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, and amino acid copolymers.

Pharmaceutically acceptable salts can also be present, e.g., mineral acid salts such as hydrochlorides, hydrobromides, phosphates, sulfates, and the like; and the salts of organic acids such as acetates, propionates, malonates, benzoates, and the like.

The pharmaceutical carriers in the pharmaceutical composition useful in the methods and articles of manufacture of this disclosure may be one or more pharmaceutical carriers suitable for topical administration. In one embodiment, the pharmaceutical carrier may be a nonionic polyoxyethylene-polyoxypropylene copolymer, also referred to as a poloxamer. The pharmaceutical carrier may be present in the pharmaceutical composition at between 5 and 25-30%. For example, the pharmaceutical carrier may be present in the pharmaceutical composition at 20% (w/w). In another embodiment the pharmaceutical carrier may be present in the pharmaceutical composition at about 22.0%. A preferred poloxamer is poloxamer 407, also known as Pluronic F-127 (BASF)

The pharmaceutical compositions for use in the methods and kits and articles of manufacture as disclosed herein may be formulated in a delayed release preparation, a slow release preparation, an extended release preparation, a controlled release preparation, and/or in a repeat action preparation to a subject with a wound characterized in whole or in part by delayed or incomplete wound healing, or other wound that does not heal at an expected rate. Such formulations are particularly advantageous for wounds that do not heal at expected rates, such as chronic wounds.

Suitable carrier materials include any carrier or vehicle commonly used as a base for creams, lotions, sprays, foams, gels, emulsions, lotions or paints for topical administration. Examples include emulsifying agents, inert carriers including hydrocarbon bases, emulsifying bases, non-toxic solvents or water-soluble bases. Particularly suitable examples include pluronics, HPMC, CMC and other cellulose-based ingredients, lanolin, hard paraffin, liquid paraffin, soft yellow paraffin or soft white paraffin, white beeswax, yellow beeswax, cetostearyl alcohol, cetyl alcohol, dimethicones, emulsifying waxes, isopropyl myristate, microcrystalline wax, oleyl alcohol and stearyl alcohol.

Slow release gels in which the anti-connexin agent is released over time are preferred for topical application. Thus, in preferred embodiments, the pharmaceutical composition may be formulated to provide sustained release of the anti-connexin agent, e.g., an anti-connexin antisense polynucleotide. Preferred anti-connexin polynucleotides include anti-connexin 43 polynucleotides, particularly anti-connexin 43 antisense polynucleotides.

Preferably, the pharmaceutically acceptable carrier or vehicle is a gel, suitably a nonionic polyoxyethylene-polyoxypropylene copolymer gel, for example, a Pluronic gel, preferably Pluronic F-127 (BASF Corp.). Such a gel can be used as a liquid at low temperatures but rapidly sets at physiological temperatures, which can assist in confining the release of the anti-connexin agent, particularly an anti-connexin antisense polynucleotide (e.g., an ODN) active ingredient, to the site of application or immediately adjacent to that site.

Other pharmaceutically acceptable carriers useful in the articles of manufacture and methods of this disclosure include an alginate, polyvinyl alcohol, hydrogels, including hydrogels that contain a cellulose derivative and/or polyacrylic acid; cellulose-based carrier, including hydroxyethyl cellulose, hydroxymethyl cellulose, carboxymethyl cellulose, hydroxypropylmethyl cellulose and mixtures thereof.

Other suitable formulations include pluronic gel-based formulations, carboxymethylcellulose(CMC)-based formulations, and hydroxypropylmethylcellulose (HPMC)-based formulations. The composition may be formulated for any desired form of delivery, including topical, instillation, parenteral, subcutaneous, or transdermal administration. Other useful formulations include slow or delayed release preparations.

The formulation that is administered may contain transfection agents. Examples of such agents include cationic agents (for example calcium phosphate and DEAE-dextran) and lipofectants (for example Lipofectam™ and Transfectam™), and surfactants.

In some embodiments, the formulation further includes a surfactant to assist with polynucleotide cell penetration or the formulation may contain any suitable loading agent. Any suitable non-toxic surfactant may be included, such as DMSO. Alternatively, a transdermal penetration agent such as urea may be included.

In some embodiments, the effective dose for a given subject preferably lies within the dose that is therapeutically effective for at least 50% of the population, and that exhibits little or no toxicity at this level.

The effective dosage of each of the anti-connexin agents employed in the methods and compositions of the invention may vary depending on a number of factors, including the particular anti-connexin agent(s) employed, the mode(s) of administration, the frequency of administration, the wound being treated, the severity of the wound being treated, the route of administration, the needs of a patient sub-population to be treated, or the needs of the individual patient which different needs can be due to age, sex, body weight, or relevant medical wound specific to the patient.

A suitable dose may be from about 0.001 mg/kg to about 10 mg/kg body weight, such as about 0.01 mg/kg to about 0.1-1.0 mg/kg body weight. A suitable dose may, however, be from about 0.001 mg/kg to about 0.1 mg/kg body weight, such as about 0.01 mg/kg to about 0.050 mg/kg body weight. Doses from about 1 to 100, 200, 300, 400, and 500 micrograms (μg) can be used, with doses of about 30 μg to about 500 μg being preferred. In other embodiments, the doses will be about 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 52.5, 55.0, 57.5, 60.0, 62.5, 65.0, 67.5, 70.0, 72.5, 75.0, 77.5, 80.0, 82.5, 85.0, 87.5, 90.0, 92.5, 95.0, 97.5, 100.0, 105, 110, 115, 120, 125, 130, 135, 140, 145, 150, 155, 160, 65, 170, 175, 180, 185, 190, 195, 200, 210, 220, 230, 250, 260, 270, 280, 290, 300, 310, 320, 330, 340, 350, 360, 370, 380, 390, 400, 410, 420, 430, 440, 450, 460, 470, 480, 490, or about 500 milligrams per square centimeter, or any range or subrange between any two of the recited doses, or any dose falling within the range of about 1.0 to about 500 milligrams per square centimeter. As noted herein, repeat applications are contemplated. Repeat applications are typically applied about once per week, or when wound-healing may appear to be stalled or slowing.

Still other useful dosage levels include those having between about 1 nanogram (ng)/kg and about 1 mg/kg body weight per day of an anti-connexin agent described herein. In certain embodiments, the dosage of each of the subject compounds will generally be in the range of about 1 ng/kg to about 1 μg/kg body weight, about 1 ng/kg to about 0.1 μg/kg body weight, about 1 ng/kg to about 10 ng/kg body weight, about 10 ng/kg to about 0.1 μg/kg body weight, about 0.1 μg/kg to about 1 μg/kg body weight, about 20 ng/kg to about 100 ng/kg body weight, about 0.001 mg/kg to about 100 mg/kg body weight, about 0.01 mg/kg to about 10 mg/kg body weight, or about 0.1 mg/kg to about 1 mg/kg body weight. In certain embodiments, the dosage of an anti-connexin agent will generally be in the range of about 0.001 mg/kg to about 0.01 mg/kg body weight, about 0.01 mg/kg to about 0.1 mg/kg body weight, about 0.1 mg/kg to about 1 mg/kg body weight, or about 1 mg/kg body weight. If more than one anti-connexin agent is used, the dosage of each anti-connexin agent need not be in the same range as the other. For example, the dosage of one anti-connexin agent may be between about 0.01 mg/kg to about 1 mg/kg body weight, and the dosage of another anti-connexin agent may be between about 0.1 mg/kg to about 1 mg/kg body weight. The dosage may also be about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 52.5, 55.0, 57.5, 60.0, 62.5, 65.0, 67.5, 70.0, 72.5, 75.0, 77.5, 80.0, 82.5, 85.0, 87.5, 90.0, 92.5, 95.0, 97.5, or about 100.0 mg per kg body weight, or any range or subrange between any two of the recited doses, or any dose falling within the range of from about 0.1 to about 100 mg per kg body weight. As noted herein, repeat applications are contemplated.

Other useful doses range from about 1 to about 10 μg per square centimeter ($\mu g/cm^2$) of wound size. Certain doses will be about 1-2, about 1-5, about 2-4, about 5-7, and about 8-10 $\mu g/cm^2$ of wound size. Other useful doses are greater than about 10 $\mu g/cm^2$ of wound size, including about 15 $\mu g/cm^2$ of wound size, about 20 $\mu g/cm^2$ of wound size, about 25 $\mu g/cm^2$ of wound size, about 30 $\mu g/cm^2$ of wound size, about 35 $\mu g/cm^2$ of wound size, about 40 $\mu g/cm^2$ of wound size, about 50 $\mu g/cm^2$ of wound size, and about 100 $\mu g/cm^2$ of wound size. Other useful doses are about 150 $\mu g/cm^2$ of wound size, about 200 $\mu g/cm^2$ of wound size, about 250 $\mu g/cm^2$ of wound size, or about 500 $\mu g/cm^2$ of wound size. As noted herein, repeat applications are contemplated.

For example, in certain embodiments, the anti-connexin agent composition may be applied at about 50 μM to about 5000 μM final concentration at the treatment site and/or adjacent to the treatment site. Preferably, the anti-connexin agent composition is applied at about 100 μM to about 3000 μM final concentration, more preferably, the anti-connexin polynucleotide composition is applied at about 150 μM to about 3000 μM final concentration, and more preferably, the anti-connexin polynucleotide composition is applied at about 150 µM to about 3300 µM final concentration. Additionally, the anti-connexin polynucleotide composition is applied at about 150 µM to about 3000 µM final concentration, and alternatively the anti-connexin polynucleotide composition is applied at about 250 µM to about 1000 µM final concentration, or at about 300 to about 1000 µM final concentration. In certain other embodiments, the anti-connexin polynucleotide is applied at about 100 µM, 200 µM, 300 µM, 400 µM, 500 µM, 600 µM, 700 µM, 800 µM, 900 µM, 1000 µM, 1100 µM, 1200 µM, 1300 µM, 1400 µM, 1500 µM, 1600 µM, 1700 µM, 1800 µM, 1900 µM, 2000 µM, 2100 µM, 2200 µM, 2300 µM, 2400 µM, 2500 µM, 2600 µM, 2700 µM, 2800 µM, 2900 µM, or about 3000 µM final concentration, or any range in between any two of these concentrations. In other embodiments, the anti-connexin agent is applied at about a 20 µM, 30 µM, 40 µM, 50 µM, 60 µM, 70 µM, 80 µM, 90 µM, 100 µM, 10-200 µM, 200-300 µM, 300-400 µM, 400-500 µM, 500-600 µM, 600-700 µM, 700-800 µM, 800-900 µM, 900-1000 or 1000-1500 µM, or 1500 µM 2000 µM, 2000-3000 µM, 3000 µM-4000 µM, 4000 µM-5000 µM, 5000 µM-6000 µM, 6000 µM-7000 µM, 7000 µM-8000 µM, 8000 µM-9000 µM, 9000 µM 10,000 µM, 10,000 µM 11,000 µM, 11,000 µM 12,000 µM, 12,000 µM 13,000 µM, 13,000 µM 14,000 µM, 14,000 µM 15,000 µM, 15,000 µM 20,000 µM, 20,000 µM 30,000 µM, 30,000 µM 50,000 µM, or greater, or any range or subrange between any two of the recited doses, or any dose falling within the range of from about 20 µM to about 50,000 µM.

Anti-connexin polynucleotide dose amounts include, for example, about 0.1-1, 1-2, 2-3, 3-4, or 4-5 micrograms (µg), from about 5 to about 10 from about 10 to about 15 µg, from about 15 to about 20 µg, from about 20 to about 30 from about 30 to about 40 µg, from about 40 to about 50 µg, from about 50 to about 75 from about 75 to about 100 µg, from about 100 µg to about 250 µg and from 250 µg to about 500 µg. Dose amounts from 0.5 to about 1.0 milligrams (mg) or more or also provided, as noted above. Dose volumes will depend on the size of the site to be treated, and may range, for example, from about 25-100 microliter (µL) to about 100-200 µL, from about 200-500 µL to about 500-1000 µL doses are also appropriate for larger treatment sites. As noted herein, repeat applications are contemplated.

Conveniently, the anti-connexin agent(s) is(are) administered in a sufficient amount to downregulate expression of a connexin protein, or modulate gap junction formation for at least about 0.5 to 1 hour, at least about 1-2 hours, at least about 2-4 hours, at least about 4-6 hours, at least about 6-8 hours, at least about 8-10 hours, at least about 12 hours, or at least about 24 hours post-administration.

The dosage of each of the anti-connexin agents in accordance with the subject invention may also be determined by reference to the concentration of the composition relative to the size, length, depth, area, or volume of the area to which it will be applied. For example, in certain topical and other applications, e.g., instillation, dosing of the pharmaceutical compositions may be calculated based on mass (e.g. micrograms) of or the concentration in a pharmaceutical composition (e.g. µg/µL) per length, depth, area, or volume of the area of application.

The initial and any subsequent dosages administered will depend upon factors noted herein. Depending on the oligonucleotide, the dosage and protocol for administration will vary, and the dosage will also depend on the method of administration selected, for example, local or topical administration.

The doses may be administered in single or divided applications. The doses may be administered once, or application may be repeated.

One or more anti-connexin agents may be administered by the same or different routes. The various agents of the invention can be administered separately at different times during the course of therapy, or concurrently in divided or single combination forms.

Preferably one or more anti-connexin agents useful for wound healing are delivered by topical administration (peripherally or directly to a site), including but not limited to topical administration using solid supports (such as dressings and other matrices) and medicinal formulations (such as gels, mixtures, suspensions and ointments). In some embodiments, the solid support comprises a biocompatible membrane or insertion into a treatment site. In another embodiment, the solid support comprises a dressing or matrix. In one embodiment of the invention, the solid support composition may be a slow release solid support composition, in which the one or more anti-connexin agent(s) useful for wound healing is(are) dispersed in a slow release solid matrix such as a matrix of alginate, collagen, or a synthetic bioabsorbable polymer. Preferably, the solid support composition is sterile or low bio-burden. In one embodiment, a wash solution comprising one or more anti-connexin polynucleotides can be used.

One or more doses may be administered to a subject having a refractory wound. In some embodiments, one or more doses of the pharmaceutical composition comprising the may be administered at appropriate intervals. In some embodiments, the pharmaceutical composition may be administered daily, two to six times per week, or weekly. For example, the composition comprising the anti-connexin agent (e.g., an anti-connexin polynucleotide) can be administered, delivered, or otherwise exposed to the wound to treated for an effective period of time, for example, at least about 0.5 hours, about 1-2 hours, about 2-4 hours, about 4-6 hours, about 6-8 hours, or for longer periods, e.g., up to 24 hours or more. Exposures of about 1-2 hour, 2-3 hour, and 4-8 hour per application or delivery is presently preferred. Alternatively, the anti-connexin agent-containing compositions and formulations described herein can be administered repeatedly, for example, once per week until healing is seen to be proceeding or is complete, as desired. For example, compositions of the invention may also be applied more frequently, 2-3 times/week. They may also be applied weekly, biweekly, or monthly. Application once or twice per week is presently preferred. The frequency of administration and dose may change over the course of treatment as the wound area and volume change. In addition, further application(s) can be made in the event wound healing once again becomes stalled or delayed.

While the delivery period will be dependent upon both the site at which the downregulation is to be induced and the therapeutic effect which is desired, continuous or slow-release delivery for about 0.5 hours, about 1-2 hours, about 2-4 hours, about 4-6 hours, about 6-8, or about 24 hours or longer is provided. In accordance with the present invention, this may be achieved by inclusion of the anti-connexin agent(s) in a formulation together with a pharmaceutically acceptable carrier or vehicle, particularly in the form of a formulation for continuous or slow-release administration.

As noted, the one or more anti-connexin agents described may be administered before, during, immediately following wounding, for example, or within about 180 or more, about 120, about 90, about 60, or about 30 days, of wounding, for example.

The routes of administration and dosages described herein are intended only as a guide since a skilled physician will determine the optimum route of administration and dosage for any particular patient and wound.

Any of the methods of treating a subject having or suspected of having or a disease, disorder, and/or wound, referenced or described herein may utilize the administration of any of the doses, dosage forms, formulations, and/or compositions herein described.

Wound Treatment

In instances of tissue damage (particularly with wounds characterized by delayed healing and chronic wounds) the formulations for use in accordance with the invention have been found effective in both promoting the wound healing process, reducing inflammation and in minimizing scar tissue formation. The formulations therefore have clear benefit in the treatment of wounds that do not heal at expected rates, whether the result of external trauma, or disease state (such as diabetic ulcers) or condition (such as venous ulcers, arterial ulcers, and vasculitic ulcers) or physical processes (such as pressure ulcers).

In one aspect the invention is directed to a method of promoting or improving wound healing in a subject suffering from or a chronic wound, delayed healing wound or incomplete healing wound, or other wounds that do not heal at expected rates, comprising administration of a therapeutically effective amount of one or more anti-connexin agents. In certain embodiments, the administration of one or more anti-connexin agents is effective to reduce granulation tissue deposition, promote cell migration to accelerate wound closure and healing, to facilitate epithelial growth, or any combination thereof.

In one aspect the invention is directed to a method of promoting or improving wound healing in a subject, comprising administration of one or more anti-connexin agents in an amount effective to regulate epithelial basal cell division and growth in a chronic wound, delayed healing wound or incomplete healing wound, or other wound that does not heal at an expected rate. In one embodiment, the anti-connexin agent is an anti-connexin antisense polynucleotide effective to regulate epithelial basal cell division and growth. In some embodiments, the anti-connexin antisense polynucleotide is an anti-connexin 26 antisense polynucleotide, an anti-connexin 43 antisense polynucleotide, or a mixture thereof.

In one aspect the invention is directed to a method of promoting or improving wound healing, comprising administration of one or more anti-connexin agents in an amount effective to regulate outer layer keratin secretion in a chronic wound, delayed healing wound or incomplete healing wound, or other wound that does not heal at an expected rate. In some embodiments, the anti-connexin agent is an anti-connexin antisense polynucleotide effective to regulate outer layer keratin secretion. In one embodiment, the connexin antisense polynucleotide is an anti-connexin 43 antisense polynucleotide, an anti-connexin 31.1 antisense polynucleotide, or a mixture thereof.

In one aspect the invention is directed to methods of reducing, preventing, or ameliorating tissue damage in a subject suffering from a chronic wound, delayed healing wound or incomplete healing wound, or other wound that does not heal at an expected rate, comprising administration of one or more anti-connexin agents.

In one aspect the invention is directed to sustained administration of one or more anti-connexin agents. In some embodiment, the anti-connexin agents are administered for at least about 1-24 hours, at least about 0.5 hours, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours or at least about 24 hours. In some embodiments, connexin expression is downregulated over a sustained period of time. Preferably, connexin 43 expression is downregulated for a sustained period of time. Conveniently, connexin 43 expression is downregulated for at least about 0.5, 1, 2, 4, 6, 8, 10, 12, or 24 hours. Full recovery of connexin expression generally occurs within at least about 48-72 hours following downregulation of expression. Suitable subjects for treatment in accordance with the invention include diabetic subjects or other subjects having a wound that does not heal at an expected rate.

In one aspect, the present invention provides methods of treating a subject having a chronic wound, delayed healing wound or incomplete healing wound, or other wound that does not heal at an expected rate, which comprises sustained administration of an effective amount of one or more anti-connexin agents. In a further aspect, the present invention provides methods of promoting or improving wound healing in a subject which comprises sustained administration of one or more anti-connexin agents to a chronic wound, delayed healing wound or incomplete healing wound, or other wound that does not heal at an expected rate.

According to another further aspect, the present invention provides methods of promoting or improving wound healing in a subject having a chronic wound, delayed healing wound or incomplete healing wound, or other wound that does not heal at an expected rate, which comprises sustained administration of one or more anti-connexin agents to a wound area in an amount effective to increase re-epithlialization rates in the wound area. In some embodiments, such methods comprise sustained administration of an anti-connexin 43 antisense polynucleotide, and/or an anti-connexin 31.1 antisense polynucleotide. In some embodiments, the composition or compositions are administered in a sustained release formulation. In other embodiments, the composition or compositions are administered for a sustained period of time. Conveniently, the composition is effective to decrease connexin 43 and/or 31.1 levels or expression for at least about 24 hours. Subjects that may be treated include diabetic subjects or other subjects having a wound that does not heal at an expected rate.

In yet another aspect, the present invention provides methods of promoting or improving wound healing in a subject having a chronic wound, delayed healing wound or incomplete healing wound, or other wound that does not heal at an expected rate, which comprises sustained administration one or more anti-connexin agents to a wound area in an amount effective to effective to regulate epithelial basal cell division and growth and/or effective to regulate outer layer keratin secretion. In one embodiment, the composition comprises an anti-connexin antisense polynucleotide effective to regulate epithelial basal cell division or growth, preferably an anti-connexin 26 antisense polynucleotide, an anti-connexin 43 antisense polynucleotide, anti-connexin 30 antisense polynucleotide or a mixture thereof, for example. In some embodiments, the composition comprises an anti-connexin antisense polynucleotide effective to regulate outer layer keratinization, preferably, an anti-connexin 31.1 antisense polynucleotide. In some embodiments, the composition or compositions are administered in a sustained release formulation. In other embodiments, the composition or compositions are administered for a sustained period of time. Conveniently, the composition is effective to decrease connexin 43, 26, and/or 30 levels or expression for at least about 24 hours. Subjects that may be treated include diabetic subjects.

In one aspect the invention is directed to methods for treatment or prophylaxis of skin wounds, including a refractory chronic wound, refractory delayed healing wound or refractory incomplete healing wound, or other refractory wound that does not heal at an expected rate, comprising administering to a subject in need thereof an effective amount of an anti-connexin agent administered to said wound or a tissue associated with said wound. In some embodiments, a composition of the present disclosure is administered to the skin or a tissue associated with the skin of said subject for an effective period of time. Conveniently, the composition is effective to decrease connexin 43 levels, or block or reduce connexin 43 hemichannel opening, for at least about 0.5 hours, about 1-2 hours, about 2-4 hours, about 4-6 hours, about 4-8 hours, about 12 hours, about 18 hours, or about 24 hours. A chronic skin wound suitable for treatment may, for example, be selected from the group consisting of pressure ulcers, diabetic ulcers, venous ulcers, arterial ulcers, vasculitic ulcers, and mixed ulcers. The chronic wound may be an arterial ulcer, which comprises ulcerations resulting from complete or partial arterial blockage. The chronic wound may be a venous stasis ulcer, which comprises ulcerations resulting from a malfunction of the venous valve and the associated vascular disease. The chronic wound may be a trauma-induced ulcer. Subjects with other ulcers may also be treated, including those with venous ulcers and others described herein and known in the art.

Compositions

The present invention is directed to pharmaceutical compositions, formulations, and their methods of manufacture and use wherein such compositions comprise a therapeutically effective amount of an anti-connexin agent, including, for example, an anti-connexin polynucleotide, including anti-connexin antisense polynucleotides. The compositions are useful in enhancing or promoting healing of wounds that do not heal at expected rates, including wounds that may be slow to heal or refractory to conventional wound treatment or wound healing promoting therapies.

In one preferred form, such compositions contain one or more anti-connexin agent species, for example, an anti-connexin antisense polynucleotide, to the mRNA or pre-mRNA of one connexin protein only. Most preferably, this connexin protein is connexin 43. Alternatively, the compositions may comprise agents, particularly polynucleotides, to more than one connexin protein. Preferably, one of the connexin proteins to which such agents are directed is connexin 43. Other connexin proteins to which anti-connexin agents may be directed include, for example, connexins 26, 30, 30.3, 31, 31.1, 32, 37, 40, and 45. Suitable exemplary polynucleotides (and ODNs) directed to various connexins are set forth elsewhere herein.

Many aspects of the invention are described with reference to anti-connexin polynucleotides, particularly oligodeoxynucleotides. However, it is understood that other suitable polynucleotides (such as RNA polynucleotides) may be used in these aspects. Other anti-connexin oligonucleotides are RNAi, siRNA, and shRNA oligonucleotides.

Accordingly, in one aspect, the invention provides compositions for use in therapeutic treatment, which comprises at least one anti-connexin agent, preferably an anti-connexin 43 polynucleotide. In certain preferred embodiments, such composition further comprise a pharmaceutically acceptable carrier or vehicle.

Kits, Medicaments and Articles of Manufacturer

Optionally, one or more anti-connexin agents may also be used in the manufacture of the medicament. In one embodiment, the medicament comprises a therapeutically effective amount of an anti-connexin agent, preferably an anti-connexin 43 polynucleotide, and a pharmaceutically acceptable carrier.

As described, the kits and packages of the invention include an article of manufacture comprising one or more containers or vessels that contains a sufficient amount of the desired anti-connexin agent(s) so that a therapeutically effective amount of such agent(s) can be delivered to a patient having a delayed healing or other chronic skin wound, for example, a chronic venous ulcer, venous stasis ulcer, arterial ulcer, pressure ulcer, diabetic ulcer, diabetic foot ulcer, vasculitic ulcer, decubitus ulcer, burn ulcer, trauma-induced ulcer, infectious ulcer, mixed ulcer, or pyoderma gangrenosum. Such kits also include instructions for the use of such agent(s). For example, such instructions may include directions regarding use for the treatment of a subject having a chronic wound or a wound characterized by delayed healing. Instructions may include instructions for use with regard to wounds that do not heal at expected rates, such as delayed healing wounds, incomplete healing wounds and chronic wounds. Such instructions provide directions regarding observing the patient to be treated in the run in period to determine if the wound is a refractory chronic wound, and, if so, directions regarding the administration of a therapeutically effective amount of a composition comprising the anti-connexin agent in the kit so as to effect treatment of the patient's wound.

In one aspect, the invention provides kits that comprise one or more compositions or formulations described herein. For example, the kit may include a composition comprising an effective amount of one or more anti-connexin 43 antisense polynucleotides.

Articles of manufacture are also provided, comprising a vessel containing a composition or formulation for use in accordance with the invention as described herein and instructions for use for the treatment of a subject. For example, in preferred embodiments the article of manufacture comprises a vessel containing an anti-connexin agent and instructions for use for the treatment of a subject suffering from a chronic, delayed healing, or incomplete healing wound, or other wound that does not heal at an expected rate.

The inventions also relate to the use of anti-connexin agents, such as anti-connexin polynucleotides, alone or in combination with transdermal patches, dressings, bandages, matrices, and coverings capable of being adhered or otherwise associated with the skin of a subject. As will be appreciated, such compositions and articles are capable of delivering a therapeutically effective amount of one or more anti-connexin agents, e.g., an anti-connexin polynucleotide such as an anti-Cx43 antisense ODN, to a delayed healing or chronic wound or the skin adjacent to such a wound.

In another aspect, the invention includes articles of manufacture comprising a vessel containing a therapeutically effective amount of one or more anti-connexin agents and instructions for use, including use for the treatment of a subject having a chronic wound or a delayed or incomplete healing wound, or other wound that does not heal at an expected rate, or a disease, disorder, and/or condition characterized in whole or in part by a chronic wound or delayed or incomplete wound healing, or other wound that does not heal at an expected rate.

As noted, wound healing has been reported to be slow in diabetes, often resulting in infection or chronic wounds that can lead to amputation. Cell-cell communication through the gap junction protein connexin 43 and the dynamic regulation of connexin 43 expression play pivotal roles in wound healing. In normal tissue, such as skin, in the first 24 hours after wounding, connexin 43 is normally downregulated and connexin 26 upregulated in keratinocytes at the edge of the wound as they adopt a migratory phenotype. However, in diabetic tissue, in general, and skin, in particular, it has been found that connexin 43 is upregulated immediately after wounding.

The examples below describe the surprising and unexpected discovery that wounds that remain within a certain size range (i.e., the "target size range") during a pretreatment phase can be more effectively and efficaciously treated than wounds that more greatly increase or decrease in size during the pretreatment phase. In particular, target size range changes during the pretreatment phase that provide for effective therapy surprisingly and unexpectedly have been discovered to range from an increase in wound size by not more than about 30% to a decrease in wound size by not more than 35% during the pretreatment phase. Preferred pretreatment phases range from about 1 to about 30 days, preferably from about 5 days to about 20 days, even more preferably from about 7 days to about 14 days.

Various aspects of the invention will now be described with reference to the following examples, which will be understood to be provided by way of illustration only and not to constitute a limitation on the scope of the invention.

EXAMPLES

Example 1—Positive Phase 2 Efficacy of an Anti Connexin Formulation in Chronic Venous Leg Ulcers This example describes the results of CoDa Therapeutics' successful Phase 2b human clinical trial. The Phase 2b Study was a randomized, parallel group, dose-ranging, controlled, double-blind Phase 2b clinical study to evaluate the safety and efficacy of a pharmaceutical formulation (Anti Connexin Formulation) comprising a single-stranded anti-connexin 43 oligo deoxyribonucleotide in 22.6% nonionic polyloxyethylene-polyoxypropylene copolymer (topically applied to patients with venous leg ulcers (VLUs) over a 10-week treatment period. The active pharmaceutical ingredient was a Cx43asODN having the nucleotide sequence of SEQ ID NO: 1. The primary purpose of the study was to determine if the can improve healing efficacy for subjects having a VLU. Secondary objectives included determining whether high or low dose Anti Connexin Formulation is safe and tolerable for VLU patients, to identify which Anti Connexin Formulation dose concentration is more effective in treating patients with VLUs, and to assess the safety and tolerability of the Anti Connexin Formulation vehicle alone (to ascertain that vehicle alone has no negative effect on compression bandaging, the standard of care (SOC)).

In the Phase 2b Study, 313 patients male and female patients aged 18 years or older were enrolled at multiple sites, and randomized in a 1:1:1:1 ratio into one of four treatment arms: low (1.0 mg/mL) or high (3.0 mg/mL) dose Anti Connexin Formulation treatment, including compression bandaging (standard-of-care (SOC)); vehicle alone, in addition to SOC; or SOC alone. Once 33 subjects were randomized into the SOC-only arm, that group was closed to recruitment and thereafter subjects were randomized on a 1:1:1 basis into the high or lose Anti Connexin Formulation or vehicle arms of the Study. Patients in the three treatment arms receiving Anti Connexin Formulation or vehicle plus SOC received once-weekly applications over a 10-week treatment period or until the first assessment of 100% VLU re-epithelialization, whichever occurred first. Reference VLU (RVLU) complete closure was defined as 100% re-epithelialization without drainage confirmed after two visits, 14 days apart. For example, when a RVLU complete closure is first observed in a particular patient (i.e., the VLU exhibits 100% re-epithelialization), the RVLU must remain closed for at least another 14 days in order for it to be confirmed as being completed closed.

The primary study endpoint was assessed as the percentage (%) change in RVLU surface area within a 10-week treatment period, as determined by photographic planimetry. Secondary study endpoints were: the time to RVLU complete closure within the 10-week treatment period; incidence of RVLU complete closure within the 10-week treatment period; incidence of RVLU complete closure at each visit within the 10-week treatment period; percentage of RVLU surface area reduction (SAR) at each visit within the 10-week treatment period; incidence of ulcer recurrence during the post-treatment period; and pain in the RVLU at each visit within the 10-week treatment period, each determined by investigator assessment, except for pain assessment, which was assessed by the particular patient on a categorical scale.

Safety assessment was based on the incidence of adverse events, as determined by investigator assessment; incidence of RVLU infection, as determined by investigator assessment; laboratory results; and physical examinations.

The Study was broken into three periods, a 2-week screening or "run-in" period (study visits S1, S2, and S3), a treatment period of up to 10 weeks (study visits T0-T10), and a post-treatment period of up to 12 weeks (study visits P0 to P5). The screening period was designed to determine whether subjects were eligible for the treatment phase of the Study. During the 10-week treatment period, high and low dose Anti Connexin Formulation or vehicle plus SOC were applied weekly using dose volumes of approximately 0.1 mL (100 uL) per 1.0 $cm^2$ of VLU surface area. For a given subject, treatment stopped at the first to occur of 10 Anti Connexin Formulation or vehicle administrations or 100% re-epithelialization of the RVLU, at which point the subject transitioned to the post-treatment period. Subjects failing to achieve 100% re-epithelialization of her/his RVLU at the T10 visit were exited from the Study, and contacted 30 days thereafter to assess for serious adverse events. The post-treatment period was intended to confirm RVLU complete closure, assess closure durability, and to continue to monitor for serious adverse events within 30 days after cessation of treatment. If a patient's RVLU was not 100% closed by the P2 visit, s/he resumed treatment. If a patient's RVLU was not 100% closed by the P3, P4, or P5 visit, s/he was thereafter exited from the Study.

At of before the first screening period visit (S1), written informed consent was obtained. At the S1 visit for each patient, a Study investigator selected a single chronic RVLU, i.e., persisting for at least 30 days prior to the S1 visit. Any RVLU clinical diagnosis was supported by venous duplex ultrasonography demonstrating venous reflux of greater than 0.5 seconds. The RVLU had to be a full thickness, well-circumscribed lesion with defined boundaries. At the end of the screening period (S3), the RVLU had to have a clean wound base free of non-viable tissue. Each RVLU had to be confirmed by review of wound photographs by a medical monitor. Patients had to have an ankle brachial index of greater than 0.80 measured at the S1 visit or within 3 months prior to the S1 visit. Any RVLU had to have a border of at least 1.5 cm of healthy skin between the outer edge of the wound bed and any surrounding skin breakdown, wound, or ulcer after debridement at the end of the S3 visit. The RVLU had to have an estimated surface area of between 2 cm$^2$ and 20 cm$^2$ at the end of the S3 visit, as determined by ruler measurement (calculated using the longest length and longest width perpendicular the longest length). Each patient had to be able to tolerate high compression bandaging (-40 mmHg at the ankle) and had to have been compliant with standardized compression bandaging over the screening period (visits S1-S3).

A subject was not eligible for enrollment if s/he had a decrease or increase greater than 40% in the estimated RVLU surface area during the 2-week screening period (to eliminate "fast healers" or those unlikely to benefit from treatment, respectively; more than 75% of the RVLU was on or below the malleous; the RVLU had been treated with continuous high compression for more than one year before the S1 visit; the RVLU wound bed had exposed bone, tendon, or fascia; the RVLU had clinical signs of infection and or biopsy proof of more than 10$^5$ organisms per gram of tissue during the screening period; the subject had cellulitis in the RVLU leg during the screening period; the RVLU had a high volume of exudate at the S1 visit that necessitates more than one high compression bandage per week; or the subject has osteomyelitis. Other standard exclusion criteria also applied, including cancer, pregnancy or breastfeeding, recent PDGF-BB, dermal substitute, or living skin treatment, being non-ambulatory, etc.

Figure 1B:
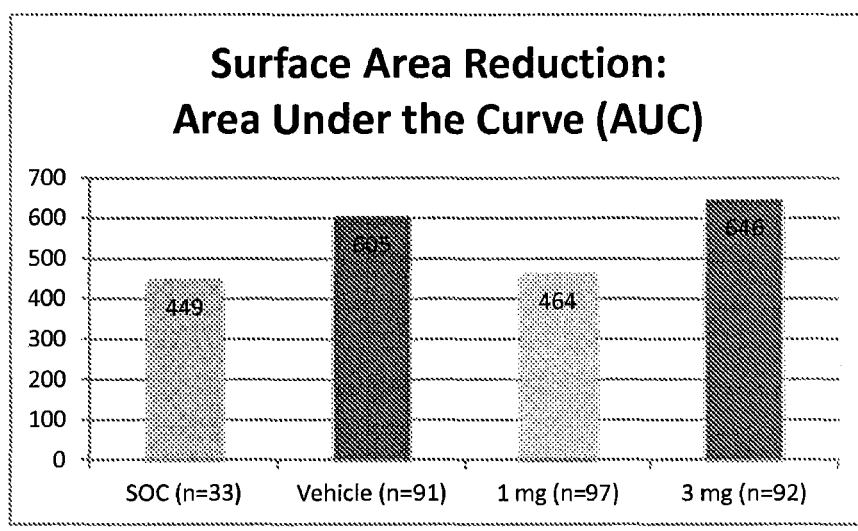
Figure 2:
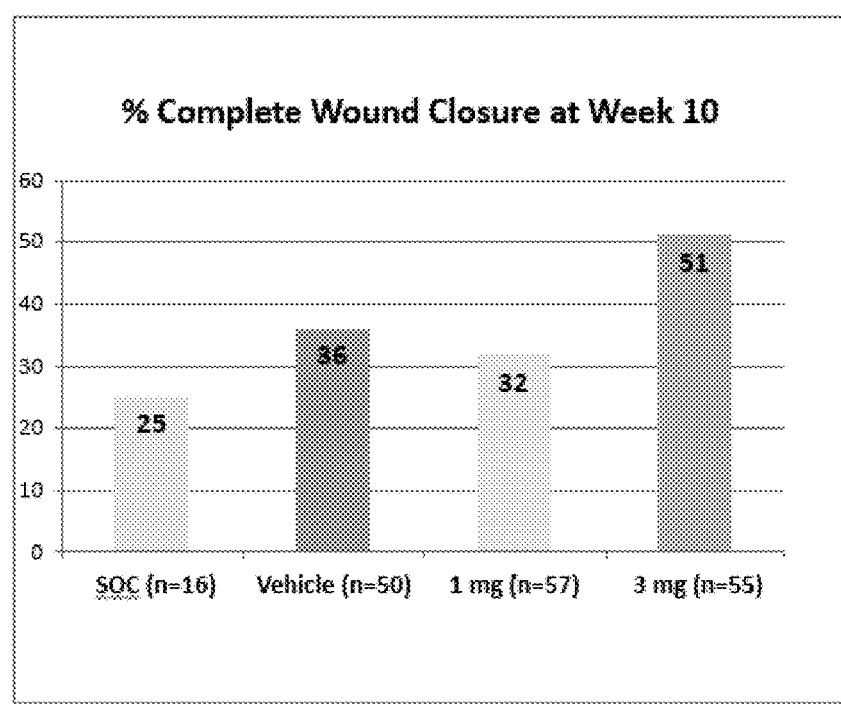
FIG. 2 shows the plot of % complete wound closure at week 10 from a re-analysis of the data from the Phase 2B study a patient subpopulation in each arm of the study that met −15% to +30% wound size change criteria.
Figure 3:
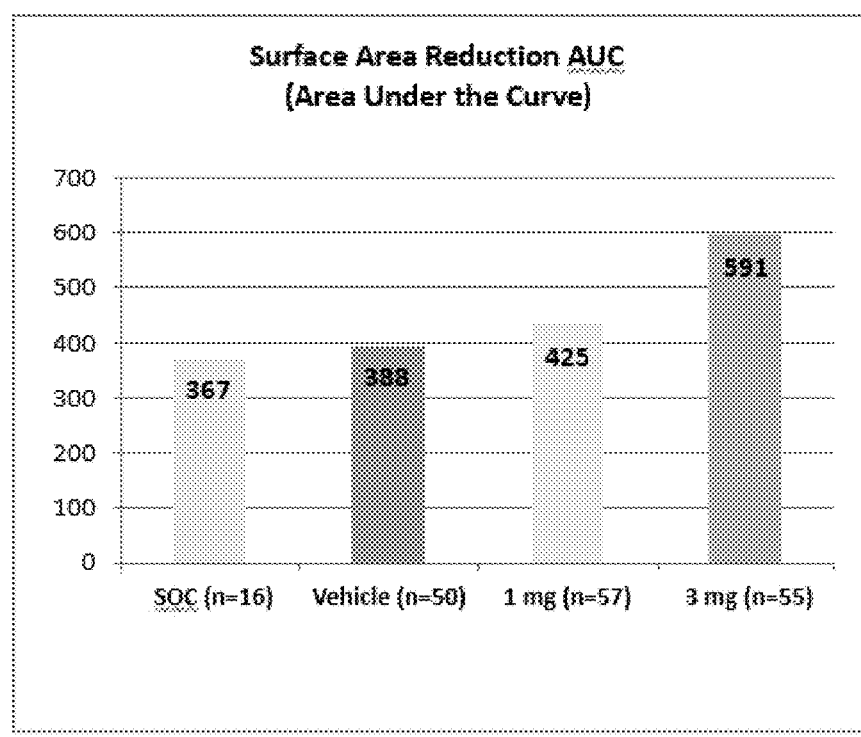
FIG. 3 shows the plot of surface area reduction based on the re-analysis of the data from the Phase 2B study for patient subpopulation that met −15% to +30% wound size change criteria in each arm of the study.

The results for Study are shown in FIGS. 1A-1C. These results show when the full Study cohort is considered, a higher than expected response rate in the vehicle-alone arm was observed. Indeed, the results from the vehicle-alone plus SOC subjects showed more complete wound closures and greater RVLU surface are reductions than observed for the low dose Anti Connexin Formulation arm. Re-analysis of the data unexpectedly revealed, in contrast to FDA guidance, that an increase or decrease of RVLU SAR of +40% to -40% surprisingly led to "rapid healers" (i.e., those who heal without the need for pharmaceutical intervention) being recruited into the study population. When a different range of RVLU SAR increase or decrease was utilized, namely -15% to +30%, a 178-patient subpopulation was identified that exhibited statistically significant (p<0.05) responses in the context of the primary SAR endpoint and the complete wound closure secondary endpoint. These results are shown in FIGS. 2, 3, and 4. This demonstrates that patients with refractory chronic wounds had statistically significant responses to treatment with the Anti Connexin Formulation. Similar efficacy responses were seen with wounds that did not decrease in size by more than about 30% (+30%) over a standard-of-care treatment period using compression bandaging over two weeks, and in wounds that did not decrease in size by more than about 35% (+35%) over the two-week compression period, in wounds that did not increase or decrease in size by more than about -5%/+30%, -10%/+30%, -15%/+30%, -20%/+30%, 25%/+30% or -30%/+30% over the two-week standard-of-care treatment period using compression bandaging.

Together, the results indicate that selecting patients for treatment with Anti Connexin Formulation benefit from pre-screening prospective patients during a pretreatment or "run-in" phase to identify patients whose chronic wounds, in this case VLUs, with surface areas that remain within a pre-determined target size range, preferably having a decrease or increase in surface are during the "run-in" period of -15% to +30%, for example. Other ranges are described herein and above. Patients having chronic wounds, e.g., VLUs, that do not more greatly increase and/or decrease in size during the "run-in" phase, from two to four weeks, when then administered an anti-connexin composition, e.g., Anti Connexin 43 Formulation in this case, can be expected to favorably respond to treatment, for example, by experiencing complete wound closure and/or by experiencing greater degrees of wound closure than would be otherwise be expected.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. The inventors (or their assignee(s)) reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation.

The methods and processes illustratively described herein suitably may be practiced in differing orders of steps, and that they are not necessarily restricted to the orders of steps indicated herein or in the claims. It is also understood that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by or on behalf of the inventors.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An article of manufacture for use in treating a refractory wound, comprising a receptacle containing a composition comprising a pharmaceutical carrier suitable for topical administration having about 20-23% of a nonionic polyoxyethylene-polyoxypropylene and about 3-30 mg/mL of an anti-connexin 43 oligodeoxynucleotide, and instructions for the treatment of the refractory wound, by topically administering the composition to or in the proximity of the wound.

2. The article of manufacture of claim 1, wherein the anti-connexin 43 oligodeoxynucleotide hybridizes to connexin 43 mRNA under conditions of medium to high stringency.

3. The article of manufacture of claim 1, wherein the anti-connexin 43 oligodeoxynucleotide has from about 15 to about 35 nucleotides and has at least about 70 percent homology to an antisense sequence of connexin 43 mRNA.

4. The article of manufacture of claim 1, wherein said nonionic polyoxyethylene-polyoxypropylene is a pluronic gel.

5. The article of manufacture of claim 1, wherein said nonionic polyoxyethylene-polyoxypropylene gel is a pluronic F-127.

6. The article of manufacture of claim 1, wherein the pharmaceutically acceptable carrier further comprises a hydrogel.

7. The article of manufacture of claim 1, wherein the hydrogel is selected from the group consisting of hydrogels containing a cellulose derivative and hydrogels containing polyacrylic acid.

8. The article of manufacture of claim 1, wherein the composition is formulated for sustained release.

9. The article of manufacture of claim 1, wherein the composition is formulated for slow release, extended release, or controlled release.

10. An article of manufacture for use in treating a refractory wound, comprising a receptacle containing a composition comprising a pharmaceutical carrier suitable for topical administration having about 20-23% of a nonionic polyoxyethylene-polyoxypropylene and about 3-30 mg/mL of an anti-connexin 30 oligodeoxynucleotide, and instructions for the treatment of the refractory wound, by topically administering the composition to or in the proximity of the wound.

11. The article of manufacture of claim 10, wherein the anti-connexin 30 oligodeoxynucleotide hybridizes to connexin 30 mRNA under conditions of medium to high stringency.

12. The article of manufacture of claim 10, wherein the anti-connexin 30 oligodeoxynucleotide has from about 15 to about 35 nucleotides and has at least about 70 percent homology to an antisense sequence of connexin 30 mRNA.

13. The article of manufacture of claim 10, wherein said nonionic polyoxyethylene-polyoxypropylene is a pluronic gel.

14. The article of manufacture of claim 10, wherein said nonionic polyoxyethylene-polyoxypropylene gel is a pluronic F-127.

15. The article of manufacture of claim 10, wherein the pharmaceutically acceptable carrier further comprises a hydrogel.

16. The article of manufacture of claim 10, wherein the hydrogel is selected from the group consisting of hydrogels containing a cellulose derivative and hydrogels containing polyacrylic acid.

17. The article of manufacture of claim 10, wherein the composition is formulated for sustained release.

18. The article of manufacture of claim 10, wherein the composition is formulated for slow release, extended release, or controlled release.

19. An article of manufacture for use in treating a refractory wound, comprising a receptacle containing a composition comprising a pharmaceutical carrier suitable for topical administration having about 20-23% of a nonionic polyoxyethylene-polyoxypropylene and about 3-30 mg/mL of an anti-connexin 26 oligodeoxynucleotide, and instructions for the treatment of the refractory wound, by topically administering the composition to or in the proximity of the wound.

20. The article of manufacture of claim 19, wherein the anti-connexin 26 oligodeoxynucleotide hybridizes to connexin 26 mRNA under conditions of medium to high stringency.

21. The article of manufacture of claim 19, wherein the anti-connexin 26 oligodeoxynucleotide has from about 15 to about 35 nucleotides and has at least about 70 percent homology to an antisense sequence of connexin 26 mRNA.

22. The article of manufacture of claim 19, wherein said nonionic polyoxyethylene-polyoxypropylene is a pluronic gel.

23. The article of manufacture of claim 19, wherein said nonionic polyoxyethylene-polyoxypropylene gel is a pluronic F-127.

24. The article of manufacture of claim 19, wherein the pharmaceutically acceptable carrier further comprises a hydrogel.

25. The article of manufacture of claim 19, wherein the hydrogel is selected from the group consisting of hydrogels containing a cellulose derivative and hydrogels containing polyacrylic acid.

26. The article of manufacture of claim 19, wherein the composition is formulated for sustained release.

27. The article of manufacture of claim 19, wherein the composition is formulated for slow release, extended release, or controlled release.

28. A method of treating a refractory wound, comprising:
   a. measuring the size of skin wound upon initial presentation for treatment to obtain a first size measurement;
   b. administering standard of care such as compression bandaging and/or off-loading to the wound;
   c. measuring the size of the wound after 2-4 weeks of administering the standard of care to obtain a second size measurement;
   d. determining that the second size indicator of the wound is within a predetermined range from about −30 to about +35% of the first size measurement, thereby identifying a refractory wound; and
   e. using the article of manufacture of claim 1.

29. The method of claim 28, wherein the pharmaceutical composition comprises a pharmaceutically acceptable carrier and an anti-connexin 43 polynucleotide present at a concentration selected from the following: from about 10-200 µM, 200-300 µM, 300-400 µM, 400-500 µM, 500-600 µM, 600-700 µM, 700-800 µM, 800-900 µM, 900-1000 or 1000-1500 µM, or 1500 µM-2000 µM, 2000 µM-3000 µM, 3000 µM-4000 µM, 4000 µM-5000 µM, 5000 µM-6000 µM, 6000 µM-7000 µM, 7000 µM-8000 µM, 8000 µM-9000 µM, 9000 µM-10,000 µM, 10,000 µM-11,000 µM, 11,000 µM-12,000 µM, 12,000 µM-13,000 µM, 13,000 µM-14,000 µM, 14,000 µM-15,000 µM, 15,000 µM-20,000 µM, 20,000 µM-30,000 µM, or from about 30,000 µM-50,000 µM.

30. A method of treating a refractory wound, comprising:
   a. measuring the size of skin wound upon initial presentation for treatment to obtain a first size measurement;
   b. administering standard of care such as compression bandaging and/or off-loading to the wound;
   c. measuring the size of the wound after 2-4 weeks of administering the standard of care to obtain a second size measurement;
   d. determining that the second size indicator of the wound is within a predetermined range from about −30 to about +35% of the first size measurement, thereby identifying a refractory wound; and
   e. using the article of manufacture of claim 10.

31. The method of claim 30, wherein the pharmaceutical composition comprises a pharmaceutically acceptable carrier and an anti-connexin 30 polynucleotide present at a concentration selected from the following: from about 10-200 µM, 200-300 µM, 300-400 µM, 400-500 µM, 500-600 µM, 600-700 µM, 700-800 µM, 800-900 µM, 900-1000 or 1000-1500 µM, or 1500 µM-2000 µM, 2000 µM-3000 µM, 3000 µM-4000 µM, 4000 µM-5000 µM, 5000 µM-6000 µM, 6000 µM-7000 µM, 7000 µM-8000 µM, 8000 µM-9000 µM, 9000 µM-10,000 µM, 10,000 µM-11,000 µM, 11,000 µM-12,000 µM, 12,000 µM-13,000 µM, 13,000 µM-14,000 µM, 14,000 µM-15,000 µM, 15,000 µM-20,000 µM, 20,000 µM-30,000 µM, or from about 30,000 µM-50,000 µM.

32. A method of treating a refractory wound, comprising:
   a. measuring the size of skin wound upon initial presentation for treatment to obtain a first size measurement;
   b. administering standard of care such as compression bandaging and/or off-loading to the wound;
   c. measuring the size of the wound after 2-4 weeks of administering the standard of care to obtain a second size measurement;
   d. determining that the second size indicator of the wound is within a predetermined range from about −30 to about +35% of the first size measurement, thereby identifying a refractory wound; and
   e. using the article of manufacture of claim 19.

33. The method of claim 32 wherein the pharmaceutical composition comprises a pharmaceutically acceptable carrier and an anti-connexin 26 polynucleotide present at a concentration selected from the following: from about 10-200 µM, 200-300 µM, 300-400 µM, 400-500 µM, 500-600 µM, 600-700 µM, 700-800 µM, 800-900 µM, 900-1000 or 1000-1500 µM, or 1500 µM-2000 µM, 2000 µM-3000 µM, 3000 µM-4000 µM, 4000 µM-5000 µM, 5000 µM-6000 µM, 6000 µM-7000 µM, 7000 µM-8000 µM, 8000 µM-9000 µM, 9000 µM-10,000 µM, 10,000 µM-11,000 µM, 11,000 µM-12,000 µM, 12,000 µM-13,000 µM, 13,000 µM-14,000 µM, 14,000 µM-15,000 µM, 15,000 µM-20,000 µM, 20,000 µM-30,000 µM, or from about 30,000 µM-50,000 µM.

* * * * *